(12) United States Patent
Borden et al.

(10) Patent No.: US 6,940,592 B2
(45) Date of Patent: Sep. 6, 2005

(54) CALIBRATION AS WELL AS MEASUREMENT ON THE SAME WORKPIECE DURING FABRICATION

(75) Inventors: Peter G. Borden, San Mateo, CA (US); Jiping Li, Fremont, CA (US); Jon Madsen, Mtn. View, CA (US)

(73) Assignee: Applied Materials, Inc., Santa Clara, CA (US)

( * ) Notice: Subject to any disclaimer, the term of this patent is extended or adjusted under 35 U.S.C. 154(b) by 498 days.

(21) Appl. No.: 09/974,571

(22) Filed: Oct. 9, 2001

(65) Prior Publication Data

US 2003/0071994 A1 Apr. 17, 2003

(51) Int. Cl.$^7$ .......................... G01J 3/28; G01N 21/00; G01N 21/55; G01N 21/86; G01B 11/28
(52) U.S. Cl. .................. 356/326; 356/237.1; 356/445; 356/630; 250/559.27
(58) Field of Search ..................... 356/237.1–237.5, 356/303, 364, 369, 445, 601, 625, 630, 300, 302, 326; 250/225, 559.27, 559.28

(56) References Cited

U.S. PATENT DOCUMENTS

| | | | |
|---|---|---|---|
| 4,201,087 A | 5/1980 | Akita et al. .................. 73/339 |
| 4,211,488 A | 7/1980 | Kleinknecht ................ 356/433 |
| 4,255,971 A | 3/1981 | Rosencwaig ................ 73/606 |
| 4,273,421 A | 6/1981 | Gurtler ........................ 356/432 |
| 4,513,384 A | 4/1985 | Rosencwaig ................ 364/563 |
| 4,521,118 A | 6/1985 | Rosencwaig .................. 374/5 |
| 4,522,510 A | 6/1985 | Rosencwaig et al. .......... 374/7 |
| 4,571,685 A | 2/1986 | Kamoshida ................ 364/468 |
| 4,579,463 A | 4/1986 | Rosencwaig et al. ........ 374/57 |
| 4,632,561 A | 12/1986 | Rosencwaig et al. ....... 356/432 |
| 4,634,290 A | 1/1987 | Rosencwaig et al. .......... 374/5 |
| 4,636,088 A | 1/1987 | Rosencwaig et al. .......... 374/5 |
| 4,652,757 A | 3/1987 | Carver ....................... 250/360 |

(Continued)

FOREIGN PATENT DOCUMENTS

| | | | |
|---|---|---|---|
| WO | 99/94880 | 12/1999 | ........... G01R/31/26 |
| WO | 00/07357 | 3/2000 | ........... G01L/21/17 |

OTHER PUBLICATIONS

Rosencwaig et al. "Detection of Thermal Waves Through Optical Reflectance", Appl Phys. Lett. 46, Jun. 1985, pp. 1013–1015.

Rosencwaig, "Thermal–Wave Imaging", SCIENCE, vol. 218, No. 4569, Oct. 1982, pp. 223–228.

Opsal et al. "Thermal–Wave Detection and Thin–Film Thickness Measurements with Laser Beam Deflection", Applied Optics, vol. 22, No. 20, Oct. 1983, pp. 3169–3176.

(Continued)

*Primary Examiner*—Zandra V. Smith
*Assistant Examiner*—Gordon J. Stock, Jr.
(74) *Attorney, Agent, or Firm*—Silicon Valley Patent Group LLP

(57) ABSTRACT

Two more measurements are made on the same workpiece, during fabrication. Each measurement may be made employing a different process. The measurements are used together to determine a property of the workpiece. For example, multiple measurements from a first process are used with a predetermined value of the property of interest in a simulator to generate a simulated value of a signal to be measured in a second process. One or more such simulated values and a measured value are used to identify a value of the property of interest. When the workpiece's property is found to not match the specification, a process control parameter used in the workpiece's fabrication is adjusted, thereby to implement process control.

11 Claims, 11 Drawing Sheets

U.S. PATENT DOCUMENTS

| | | | |
|---|---|---|---|
| 4,750,822 A | 6/1988 | Rosencwaig et al. | 324/445 |
| 4,854,710 A | 8/1989 | Opsal et al. | 356/432 |
| 4,952,063 A | 8/1990 | Opsal et al. | 356/432 |
| 4,996,659 A | 2/1991 | Yamaguchi et al. | 714/736 |
| 5,034,611 A | 7/1991 | Alpern | 250/372 |
| 5,042,952 A | 8/1991 | Opsal et al. | 356/432 |
| 5,074,669 A | 12/1991 | Opsal | 356/447 |
| 5,159,412 A | 10/1992 | Willenborg et al. | 356/445 |
| 5,181,080 A | 1/1993 | Fanton et al. | 356/381 |
| 5,228,776 A | 7/1993 | Smith et al. | 374/5 |
| 5,229,304 A | 7/1993 | Chang et al. | 437/7 |
| 5,377,006 A | 12/1994 | Nakata | 356/349 |
| 5,379,109 A | 1/1995 | Gaskill et al. | 356/445 |
| 5,454,004 A | 9/1995 | Leger | 372/99 |
| 5,652,716 A | 7/1997 | Battersby | 703/13 |
| 5,657,754 A | 8/1997 | Rosencwaig | 128/633 |
| 5,706,094 A | 1/1998 | Maris | 356/432 |
| 5,741,614 A | 4/1998 | McCoy et al. | 430/30 |
| 5,761,082 A | 6/1998 | Miura-Mattausch | 703/14 |
| 5,764,363 A | 6/1998 | Ooki et al. | 356/364 |
| 5,877,860 A | 3/1999 | Borden | 356/376 |
| 5,883,518 A | 3/1999 | Borden | 324/752 |
| 5,966,019 A | 10/1999 | Borden | 324/752 |
| 5,978,074 A | 11/1999 | Opsal et al. | 356/72 |
| 6,020,964 A | 2/2000 | Loopstra et al. | 356/500 |
| 6,049,220 A | 4/2000 | Borden et al. | 324/765 |
| 6,054,868 A | 4/2000 | Borden et al. | 324/752 |
| 6,113,733 A * | 9/2000 | Eriguchi et al. | 156/345.24 |
| 6,118,533 A | 9/2000 | Banet et al. | 356/345 |
| 6,154,280 A | 11/2000 | Borden | 356/376 |
| 6,169,601 B1 | 1/2001 | Eremin et al. | 356/240 |
| 6,211,961 B1 | 4/2001 | Maris | 356/432 |
| 6,268,916 B1 | 7/2001 | Lee et al. | 356/432 |
| 6,281,027 B1 | 8/2001 | Wei et al. | 438/14 |
| 6,323,951 B1 | 11/2001 | Borden et al. | 356/502 |
| 6,327,035 B1 | 12/2001 | Li et al. | 356/432 |
| 6,400,454 B1 | 6/2002 | Noguchi et al. | 356/237 |
| 6,426,644 B1 | 7/2002 | Borden et al. | 324/765 |
| 6,476,920 B1 | 11/2002 | Scheiner et al. | 356/630 |
| 6,483,594 B2 | 11/2002 | Borden et al. | 356/502 |
| 6,486,965 B1 | 11/2002 | Kim | 356/626 |
| 6,489,624 B1 | 12/2002 | Ushio et al. | 250/559 |
| 6,489,801 B1 | 12/2002 | Borden et al. | 324/766 |
| 6,694,284 B1 * | 2/2004 | Nikoonahad et al. | 702/155 |
| 6,734,968 B1 * | 5/2004 | Wang et al. | 356/369 |
| 6,804,003 B1 * | 10/2004 | Wang et al. | 356/369 |
| 2001/0015937 A1 | 8/2001 | Yamaguchi et al. | 369/13 |
| 2002/0126732 A1 | 9/2002 | Shakouri et al. | 374/130 |
| 2003/0096436 A1 | 5/2003 | Satya et al. | 438/11 |
| 2004/0218180 A1 * | 11/2004 | Rosencwaig et al. | 356/369 |

OTHER PUBLICATIONS

Rosencwaig, "Thermal Wave Characterization and Inspection of Semiconductor Materials and Devices", Chapter 5 (pp. 97–135) of Photoacoustic and Thermal Wave Phenomena in Semicondutors, North Holland (month unavailable) 1987.

Constantinos Christofides "Photomodulated Thermoreflectance Investigation of Semiconducting Implanted Wafers," Microelectronic Engineering, 40 (1998), 251–261.

W. L. Smith et al. "Ion Implant Monitoring With Thermal Wave Technology," Nuclear Instruments and Methods Physics Research, B21, (1987), 537–541.

J. Opsal, "High Resolution Thermal Wave Measurements and Imaging of Defects and Damage in Electronic Materials" Photoacoustic and Photothermal Phenomena II, Springer Series in Optical Sciences, vol. 62, Springer Verlag Berlin, Heidelberg, 1990.

Jon Opsal, "Modulated Interference Effects and Thermal Wave Monitoring of High–Dose Ion Implantation in Semiconductors," Review of Progress in Quantitative Nondestructive Evaluation, vol. 8B, Plenum Publishing Corporation, 1989.

*Quality Today News*, article entitled "In–Line Metrology SEM System with 3D Imaging" dated Jan. 10, 2000 and published at http://www.qualitytoday.com/Jan–00–news/011000–3.htm before Apr. 4, 2001.

Bristow, Thomas C. and Dag Lindquist, "Surface Measurements With A Non–Contact Nomarski–Profiling Instrument", Interferometric Metrology, SPIE vol. 816, Aug. 1987, pp. 106–110.

"Process Monitoring System", Quantox Product Brochure, 3 pages, published prior to Mar. 1, 2002.

A. Rosencwaig, "Thermal Wave Measurement of Thin–Film Thickness", 1986 American Chemical Society, pp. 182–191.

A. Rosencwaig et al., "Thin–Film Thickness Measurements with Thermal Waves", Journal De Physique, Oct. 1983, pp. C6–483—C6–489.

W. L. Smith et al. "Thermal–wave Measurements and Monitoring of TaSIx Silicide Film Properties" J. Vac. Technol.B2(4), Oct.–Dec. 1984, pp. 710–713.

L. Chen et al., "Thermal Wave Studies of Thin Metal Films Using the Meta–Probe–A New Generation Photothermal System" 25th Review of Progress in QNDE, Snowbird, UT Jul. 19–24, 1998, pp. 1–12.

J. Opsal, "The Application of Thermal Wave Technology to Thickness and Grain Size Monitoring of Aluminum Films", SPIE vol. 1596 Metalization Performance and Reliability Issues for VLSI and ULSI (1991), pp. 120–131.

A. Rosencwaig, "Process Control In IC Manufacturing With Thermal Waves", Review of Progress in Quantitative Nondestructive Evaluation, vol. 9, 1990, pp. 2031–2037.

Per–Eric Nordail et al. "Photothermal Radiometry", Physica Scripts, vol. 20, 659–662, 1979.

A. Rosencwaig, "Thermal Wave Monitoring and Imaging of Electronic Materials and Devices", pp. 73–109.

A. Rosencwaig, "Applications of Thermal–Wave Physics to Microelectronics", VLSI Electronics, Microstructure Science vol. 9, 1995, pp. 227–288.

W. Lee Smith et al., "Voids, Notches and Micros=cracks in A 1 Metallization Detected by Nondestructive Thermal Wave Imaging", Jun. 23m, 1989, pp. 211–221.

W. Lee Smith et al., Imaging of Subsurface Defects in ULSI Metallization (AI Voids SI Precipitates, Silicide Instability) and SI Substrates (D Defects), Technical Proceedings Simicon/Japan 1992, Nippon Convention Center, Japan, pp. 238–246.

W. Lee Smith, "Nondestructive Thermal Wave Imaging of Voids & Microcracks in Aluminum Metallization", 1989 WLR Final Report, pp. 55–68.

W. Lee Smith, "Direct Measurement of Stress–Induced Void Growth by Thermal Wave Modulated Optical Reflectance Imaging", 1991 IEEE/IRPS, pp. 200–208.

W. Lee Smith, "Evaluating Voids and Microcracks in A 1 Metallization", Semiconductor International, Jan. 1990, pp. 232–237.

C. G. Welles et al., "High–Resolution Thermal Wave Imaging of Surface and Subsurface Defects in IC Metal Lines", Materials Research Society, SF Marriott, Apr. 27–May 1, 1992, pp. 1187–1191.

L. Chen et al., "Meta–Probe: A New Generation Photothermal System For Thin Metal Films Characterization"(believed to be prior to Mar. 1, 2002).

L. Chen et al., "Thermal Wave Studies of Thin Metal Films and Structures", (believed to be prior to Mar. 1, 2002).

R. S. Sharpe, Research Techniques in Nondestructive Testing vol. VII, Academic Press 1984, pp. 158–365.

R. L. Thomas et al., "Thermal Wave Imaging For Nondestructive Evaluation" 1982 Ultrasonic Symposium, pp. 586–590.

G. Slade Cargill III, "Electron–Acoustic Microscopy", Physics Today, Oct. 1981, pp. 27–32.

A. Rosencwaig, "Thermal Wave Microscopy", Solid State Technology, Mar. 1982, pp. 91–97.

Eric A. Ash, "Acoustical Imaging" vol. 12, Plenium Press, Jul. 19–22, 1982, pp. 61–65.

Paquin, "Properties of Metals", Handbook of Optics, vol. II, McGraw–Hill, Inc. (month unavailable), 1995, pp. 35.3–35.7.

Amritharaj and Seiler, "Optical Properties of Semiconductors", Handbook of Optics, vol. II, McGraw–Hill, Inc. (month unavailable), 1995, pp. 36.67–36.68, 36.95 and Table 11.

Walter G. Driscoll and William Vaughan, "Handbook of Optics", 1978, pp. 8–42, 8–43, 8–107, and 10–72 to 10–77.

* cited by examiner

CALIBRATION AS WELL AS MEASUREMENT ON THE SAME WORKPIECE DURING FABRICATION

CROSS-REFERENCE TO RELATED APPLICATIONS

This application is related to and incorporates by reference herein in their entirety, the following commonly owned, copending U.S. patent applications:

Ser. No. 09/799,481, entitled "USE OF A COEFFICIENT OF A POWER CURVE TO EVALUATE A SEMICONDUCTOR WAFER" filed Mar. 5, 2001, by Peter G. Borden et al;

Ser. No. 09/544,280, entitled "APPARATUS AND METHOD FOR EVALUATING A WAFER OF SEMICONDUCTOR MATERIAL," filed Apr. 6, 2000, by Peter G. Borden et al which is a continuation of Ser. No. 09/095,804 filed Jun. 10, 1998;

Ser. No. 09/274,821, entitled "APPARATUS AND METHOD FOR DETERMINING THE ACTIVE DOPANT PROFILE IN A SEMICONDUCTOR WAFER," filed Mar. 22, 1999, by Peter G. Borden et al.;

Ser. No. 09/521,232, entitled "EVALUATING A PROPERTY OF A MULTILAYERED STRUCTURE" filed Mar. 8, 2000, by Peter G. Borden et al; and Ser. No. 09/788,273, entitled "EVALUATING SIDEWALL COVERAGE IN A SEMICONDUCTOR WAFER" Feb. 16, 2001, by Peter G. Borden et al.

BACKGROUND

In a damascene process, a stack of dielectric layers is first laid down on a semiconductor substrate that includes underlying layers of devices and interconnects, to form a structure that is eventually cut into multiple dies. The dielectric layers serve various functions, such as anti-reflection coating, insulating and etch-stopping. Grooves are then etched in the dielectric stack. The grooves are then filled with a conductive metal such as copper using a process such as plating. Finally, an exposed surface of the resulting structure is polished, to leave metal lines inlaid within the grooves.

There are several methods for measuring thickness, or change in thickness, of an upper-most layer in which the metal lines are formed. For example, in a method called "stylus profilometry" a stylus is run along the exposed surface and the height of the stylus is measured. This method requires contact to the surface of the structure and also requires that the substrate be precisely level prior to the damascene process. In addition, the stylus tips are fragile and require frequent replacement. As another example, focused ion beam scanning electron micrography (FIB-SEM) uses a focused ion beam to cut a hole in the structure. A scanning electron micrograph is then used to image the exposed cross-section. In a related method, the focused ion beam is used to cut out a section, which is then viewed with a transmission electron microscope (TEM). Such methods are slow, destructive, and not suited for monitoring the fabrication process.

Dielectric film thickness is also measured using ellipsometry. In one such method, light at multiple wavelengths is shone on a surface at an angle and the reflection is measured as function of incident polarization angle. Applicants note that a measurement made by this method uses a large spot size because a source of white light cannot be focused to the diffraction limit of a single wavelength. Applicants further note that ellipsometry does not provide the resolution required to measure profiles that vary across a distance (e.g. 20 $\mu$m) that is of the same order of magnitude as the spot size. Applicants also note that use of polarization as part of ellipsometry means polarization cannot be used to obtain measurements of dielectric properties within an array of metal lines.

U.S. Pat. No. 5,978,074 (which is incorporated by reference herein in its entirety) discloses an apparatus for characterizing multilayer samples. The apparatus focuses an intensity modulated pump beam onto the sample surface to periodically excite the sample, and also focuses a probe beam onto the sample surface within the periodically excited area. The power of the reflected probe beam is measured by a photodetector. The output of the photodetector is filtered and processed to derive the modulated optical reflectivity of the sample. Measurements are taken at a plurality of pump beam modulation frequencies. In addition, measurements are taken as the lateral separation between the pump and probe beam spots on the sample surface is varied. The measurements at multiple modulation frequencies and at different lateral beam spot spacings are used to help characterize complex multilayer samples. In the preferred embodiment, a spectrometer is also included to provide additional data for characterizing the sample.

Regarding use of a spectrometer, U.S. Pat. No. 5,978,074 states (at column 9, line 58 to column 10, line 10) "In the preferred embodiment, the subject apparatus further includes a spectrometer for providing additional data. As noted above, a white light source 120 is necessary for illuminating the sample for tracking on a TV monitor. This same light source can be used to provide spectral reflectivity data. As seen in FIG. 1, a beam splitter can be used to redirect a portion of the reflected white light to a spectrometer 142. The spectrometer can be of any type commonly known and used in the prior art. FIG. 4 illustrates one form of a spectrometer. As seen therein, the white light beam 122 strikes a curved grating 242 which functions to angularly spread the beam as a function of wavelength. A photodetector 244 is provided for measuring the beam. Detector 244 is typically a photodiode array with different wavelengths or colors falling on each element 246 in the array. The outputs of the diode array are sent to the processor for determining the reflectivity of the sample as a function of wavelength. This information can be used by the processor during the modeling steps to help further characterize the sample."

Use of the white light for aligning the sample implies that the spectrometer is shown through the measurement objective lens. This is because the view for alignment must be the same as the view for measurement. Therefore, the spectrometer must be combined with the two laser measurement, adding complexity.

Applicants note that U.S. Pat. No. 5,978,074 is silent on how to "further characterize the sample," other than to describe determining the sample's reflectivity as a function of wavelength as noted above. Applicants further note that U.S. Pat. No. 5,978,074 is also silent on what is done after a sample has been "further" characterized.

U.S. Pat. No. 5,978,074 also cites U.S. Pat. No. 5,074,669 granted to Opsal, which discloses using the combination of modulated optical reflectance plus the non-modulated reflectance of the two lasers to evaluate the implant dosage level in the semiconductor sample or to measure the thickness of a layer created by implantation.

According to an article entitled "Modules Are In, But Supertools Endure" by Alexander E. Braun in Semiconductor International November 1999 available on the Internet at www.semiconductor.net/semiconductor/issues/issues/1999/nov99/docs/imt.asp describes use of an ellipsometer in combination with a spectroscopic reflectometer. Specifically, the article states "The recently introduced Rudolph S200 system, for example, uses a proprietary multi-angle laser ellipsometer for thin films. The ellipsometer also is very sensitive to etch-to-zero applications, and yet tolerant of refractive index changes in underlying materials. The ellipsometric measurements also can be combined with a spectroscopic reflectometer and provide a better capability to measure overetch and characterize polish rate across the entire process window at more than 100 wafers per hour (five sites per wafer) . . . Rudolph has eliminated the primary cause of long-term difficulty in obtaining ellipsometer repeatability. If a microspot lens ellipsometer is used to measure on-product or a small spot, and high repeatability is attempted, stress birefringence in the lens—slight temperature changes over time—causes thickness measurements to vary by a few tenths of an Ångstrom. The new capability circumvents this, providing 0.01 Å repeatability."

SUMMARY

In accordance with the invention, two or more measurements are made on the same workpiece, during fabrication of the workpiece, and one of the measurements is used to calibrate another of the measurements. In one embodiment, each measurement is made employing a different process, and the measurements are used together to determine a property (also called "property of interest") of the workpiece. The multiple measurements may be made at two or more locations on the workpiece that are separated from one another, or alternatively even at the same location as long as different measurement processes are used. If the same process is used, the measurements locations.

In one embodiment, multiple measurements from a first process are used with a predetermined value of the property of interest in a simulator to generate a simulated value of a signal to be measured in a second process. One or more such simulated values and a measured value are used together, to identify a value of the property of interest.

If the workpiece's property value is found to not match the specification, a process control parameter used in fabrication of the in the workpiece is adjusted, thereby to implement process control. If the workpiece's property value does match the specification, fabrication of the workpiece is continued (i.e. workpiece is not rejected) and the process control parameter is left unchanged. In some fabrication processes, only one parameter varies with the process (such as the thickness of the top layer of a film). In such fabrication processes, in one embodiment, a calibration measurement is made as described above to determine the properties of a structure, and then another measurement (such as a single wavelength measurement) is used to determine the thickness change of only the top layer.

DETAILED DESCRIPTION

Figure 1A:
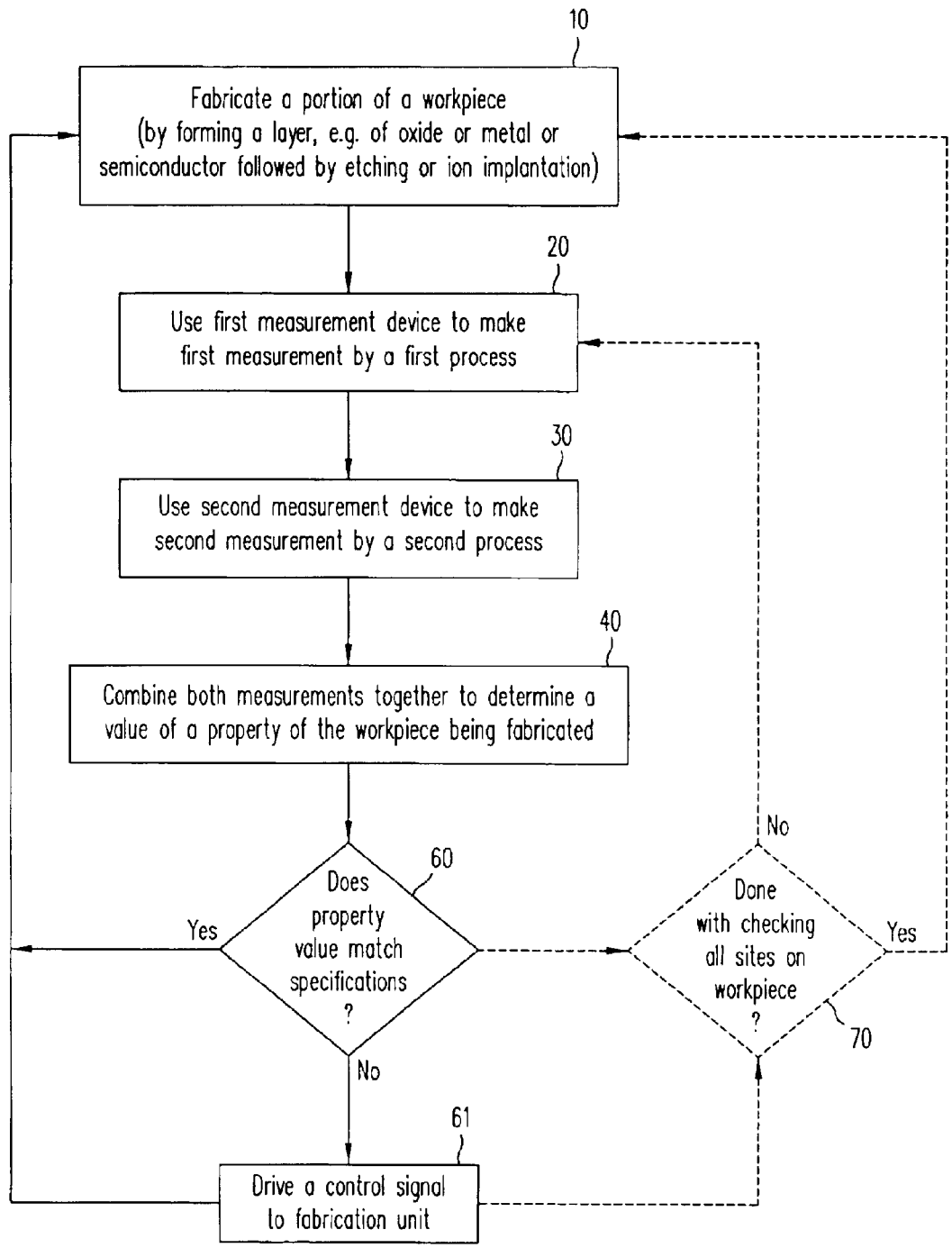
FIG. 1A illustrates, in a flow chart, use of multiple measurement devices to determine a property, and to control fabrication of a workpiece, in accordance with the invention.

In accordance with the invention, a portion of a workpiece is fabricated (see act 10 in FIG. 1A), at least two measurements are made on the same workpiece (see acts 20 and 30 in FIG. 1A). The measurements are combined (e.g. one measurement used to calibrate another measurement) to determine a value of a property of the workpiece. If the property value falls outside of specifications for the workpiece, a process control parameter used in fabrication is changed in real time.

Any kind of workpiece may be fabricated in the manner described herein, including, for example, a wafer (also called "semiconductor substrate") of semiconductor material that is fabricated in a wafer fabrication system 100 (FIG. 1B) to form a "patterned wafer", and that is eventually cut into integrated circuit dies. Other workpieces that may be fabricated as described herein include silicon-on-insulator wafers, printed circuits, multi-layer ceramics, hybrid microcircuits.

Figure 1B:
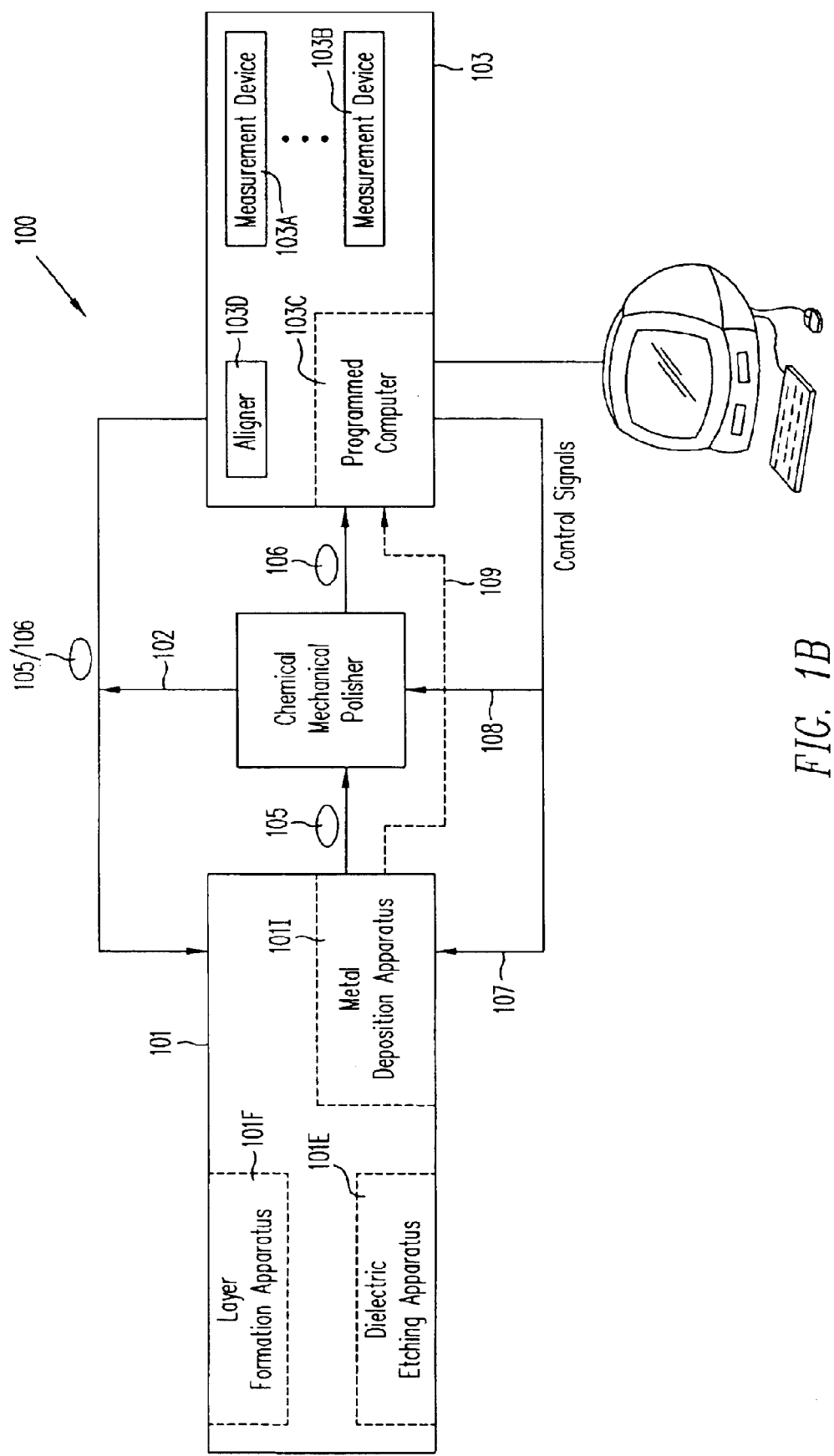
FIG. 1B illustrates, in a block diagram, an apparatus that implements the method of FIG. 1A for a wafer of semiconductor material as the workpiece.

Any fabrication process and/or device well known in the art may be used to prepare a patterned wafer prior to measurement, including, e.g. layer formation by chemical vapor deposition (CVD) and/or etching of metal, rapid thermal annealing (RTA), and/or chemical mechanical polishing (CMP). For example, FIG. 1B illustrates use of a layer formation apparatus 101F, dielectric etching apparatus 101E, and metal deposition apparatus 101I that are used with a chemical mechanical polisher 102 to form the patterned wafer. Although not specifically illustrated in FIG. 1B, any conventional devices used in fabrication of a wafer, e.g. for photoresist application/exposure/resist strip may be used instead of or in addition to device 101 in a system 100 as described herein.

System 100 also includes a metrology tool 103 that measures various material properties in a patterned wafer 106. Although wafer 106 is illustrated as having been polished, metrology tool 103 may be used even with unpolished wafers 105, as illustrated by path 109 in FIG. 1B.

Depending on the embodiment, the multiple measurements may all be made employing a common device and/or process, or each such measurement may be made by a different device/process. If a common measurement device or a common measurement process is used, such measurements are made with different resolutions and/or precision, and/or in different locations of the same workpiece. Resolution relates to the size of features that can be resolved, while precision determines how accurate a measurement is (the standard deviation of the measurement result). For example, it may be necessary to resolve two spatial features separated by 5 μm. Each feature may have to be measured to a precision of ±10 nm in depth.

Alternatively, different measurement devices and different measurement processes may be used for each of the measurements, and if so the measurements may have the same resolution or different resolutions. For example, an area over which the measurements are made may be of different sizes in the measurements. Moreover, if the measurement devices and processes are different, some (but not all) of the measurements may be made in a destructive manner, if made in a test area (also called "test pattern") of the patterned wafer.

Therefore, a low resolution (and possibly destructive) method may be used to make a multi-variable (several film) measurement in a test area, and the results of such measurement applied to an area of interest in which only one property changes, and the change in property is measured in the area of interest using a high resolution method. Even though the high resolution method is capable of measuring only one (or a small subset) of the properties measured by the low resolution method, the high resolution method is used in combination with the low resolution method as described herein. In one embodiment of the invention the reference measurement is done through a separate low powered measurement device (e.g. a spectrometer) that is not part of the optical train for the final measurement. In this embodiment, a low power objective may be used for coarse alignment (for example, to find a die or large feature), but not for final alignment (for example, to find a measurement site within a die).

As noted above, instead of low and high resolution methods, destructive and non-destructive methods may be used in the test area and area of interest respectively. Also, as would be apparent to the skilled artisan in view of this disclosure, any two methods and/or devices that are not suitable for use in one of the two kinds of areas (e.g. test area and area of interest) may be used in combination, when the two areas are sufficiently near one another for the properties that affect the measurements to remain substantially the same (e.g. change by no more than 1%). Examples of such combinations of methods include:

| Reference | Site | Active area measurement |
| --- | --- | --- |
| Thickness of stack | Test pattern | Thickness of top layer |
| Dielectric tkns | Test pattern | Doping, junction depth |
| SIMS doping profile | Test pattern | Junction depth uniformity |
| Linewidth | Test array | Width of single line |

Furthermore, instead of combining measurements from just two methods and/or devices, measurements from any number of methods and/or devices may be combined as described herein. For example, doping level of an ion implant may be characterized with a rapid non-destructive, high-resolution method, as follows. The measurement region has a silicon dioxide coating (known as a screen oxide). A test area is measured with a reflectometer to determine the screen oxide thickness. A SIMS measurement (slow method allows measurement at only one site—say at the wafer center) is also made in a test area to determine a reference doping concentration. The screen oxide thickness and reference concentration are used to calibrate the third measurement that has high speed that is then applied at a large number e.g. 49 sites on the wafer to determine uniformity of the doping.

In the embodiment illustrated in FIG. 1B, metrology tool 103 includes an aligner 103D that positions a wafer to be measured in one of measurement devices 103A and 103B, and a programmed computer 103C determines a value of a property of the wafer based on multiple measurements by one or more of devices 103A and 103B. Note that a single aligner 103D is used in one embodiment to position the wafer in all measurement devices of tool 103, so that properties at locations that are coincident with one another or adjacent to one another within a predetermined distance are measured.

However, a reference measurement may be made on a separate thin-film measuring system and then the high resolution measurement on a second system that is separate and distinct. Therefore, in an alternative embodiment, each measurement device has its own aligner.

Measurements as described herein may be made by any of a number of measurement processes and/or devices well known in the prior art. For example, one measurement may be made by a spectroscopic reflectometer (well known in the prior art) to determine a number of properties (such as thicknesses, refractive indices and absorption constants of one or more films of, e.g. oxides, nitrides, poly and a-silicon and polyimide), and another measurement may be made by a laser reflectometer (also well known in the prior art), to more precisely measure a property of interest.

In the just-described example, the spectroscopic reflectometer has a larger spot size than the laser reflectometer. Specifically, a single wavelength laser (of the type normally used in a laser reflectometer) is collimated and coherent and can be focused to a much smaller spot (on the order of 1 $\mu$m) as compared to a beam of white light (of the type normally produced by an incandescent bulb which is commonly used in a spectroscopic reflectometer).

Instead of a spectroscopic reflectometer, other tools (such as PQ Ruby and PQ Emerald available from Philips Analytical Inc. 12 Michigan Drive, Natick, Mass. 01760) may be used. For example, an acoustic tool, a 4-point probe, a scanning electron microscope, a stylus profilometer or an X-Ray machine may be used to perform a calibration measurement. Calibration measurements may be made using the Opti-Probe film thickness measurement tool, available from Therma-Wave, followed by a second measurement using Therma-Probe ion implant dose measurement system. Alternatively, measurement of film thickness may be made by use of KLA UV-1050, or Rudolph SpectraLaser.

Commercially available devices that can be used for a first measurement include:

| 1. | KLA-Tencor | ASET-F5x, UV-1280SE, UV-1080 |
| --- | --- | --- |
| 2. | Rudolph | S 200, S 300, SpectraLASER 200 and 300 |
| 3. | Nanometrics | 8300X, 9300 |
| 4. | Therma-Wave | Opti-Probe 3290, 3290DUV, 5240 |
| 5. | Cameca | IMS 6f (SIMS) |
| 6. | Physical Electronics Adept 1010 (SIMS) | |

Any of these devices 1–6 can be used for a calibration measurement. In addition, commercially available devices that can be used for a second measurement include:

| 7. | Therma-Wave | Therma-Probe TP-500, TP-630 |
| --- | --- | --- |
| 8. | Boxer Cross | BX-10 |
| 9. | Boxer Cross | BX-30 |

Measurements from the above-described devices can be combined as follows: (A) measurements from any of 1–4 can be combined with 9 (dielectric film thickness measurement can be combined with high resolution dielectric film thickness of top layer); (B) measurements from any of 1–4 combined with 7 or 8 (overlaying dielectric film measurement with measurement of ion implant dose); and (C) measurements from any of 5–6 combined with 8 (doping profile measurement combined with junction depth uniformity).

In several different embodiments, the following combination of methods are used:

| First measurement | Second measurement |
| --- | --- |
| Reflectometry, ellipsometry | Laser reflectance |
| SIMS | Dose, junction depth measurement (2 laser reflectance) |
| Four point probe | Dose measurement (2 laser reflectance) |
| Acoustic metal thickness | Thickness of whole stack as per U.S. Pat. No. 6,054,868 |
| Scatterometry CD | Linewidth dependence as described in U.S. Pat. No. 6,054,868. |

The acoustic metal thickness measurement is used in e.g. the Rudolph MetaPULSE to measure the thickness of each layer in a metal stack, with a spot size of 7–10 μm. This could be coupled with the method of U.S. Pat. No. 6,054,868 to measure changes in the thickness of the stack as a whole (without resolving individual layers) but in fine patterns or with higher spatial resolution.

Scatterometry measures critical dimensions (CD) but needs about a 50 μm spot to do so. The method described in U.S. Pat. No. 6,054,868 is sensitive to line width, where the spot may be only 2 μm wide.

Regardless of the process and/or device used in measurement, multiple measurements of the type described herein are made on the same workpiece in accordance with the invention, and are used together (see act 40 in FIG. 1A) to determine a value of a property (also called "property of interest") of the workpiece. Various kinds of measurements from the same workpiece may be combined in any manner to obtain the property value.

If a workpiece's property value, which has been determined by combination of the measurements as described above, is found to not match the specification (see act 60 in FIG. 1A), a process control parameter used in the workpiece's fabrication is adjusted (see act 61 in FIG. 1A), thereby to implement process control. Such a workpiece may be discarded (because property value doesn't match specification). If the workpiece's property value matches specification (e.g. falls within a specified tolerance around a specified value), the workpiece is processed further, i.e. another portion of the workpiece is fabricated (e.g. by returning to act 10 in FIG. 1A).

Depending on the embodiment, the above-described acts 20–61 for measuring the property of interest may be repeated (as illustrated by act 70 in FIG. 1A) at a number of locations, e.g. to determine a profile of the property of interest radially across the workpiece or around the circumference if the workpiece has a circular shape. In such embodiments, the profile is used in determining whether or not a workpiece under fabrication matches the specification.

In a first example all measurements are of the same property, and a first measurement on the in-fabrication-workpiece is used to calibrate a second measurement on the same workpiece. In such an example, identical measurement methods may be used, at different sites of the workpiece. In a second example, the following measurements are made on the same workpiece: a first measurement is of a different property from a second measurement, and the first measurement is used in a simulator (e.g. a personal computer programmed with simulation software) to generate a simulated value for the second measurement, and the simulated value is then used to calibrate the second measurement.

In a third example, the following measurements are made on the same workpiece: a first measurement is used to generate a set of simulated values for a second measurement, based on a set of predetermined values of the property that the workpiece is likely to have, and the second measurement is used to identify the closest simulated value which is then used to determine the property. For convenience, in the following description a first measurement of any of the just-described three examples is referred to as "calibration measurement" (even though calibration is not performed in the third example), and the second measurement is referred to as "actual measurement".

The multiple measurements on a workpiece being fabricated as described above can be made at the same location, or at different locations. When the measurements are made at different locations, the locations are selected to ensure that one or more properties that may affect any of the measurements, other than a property of interest, are substantially identical (e.g. differ by no more than 1%) between the locations. Under such conditions, the multiple measurements when combined as described herein identify any local variations (i.e. variations between the locations) that are caused by the process being used to fabricate the portion of the workpiece.

Figure 2A:
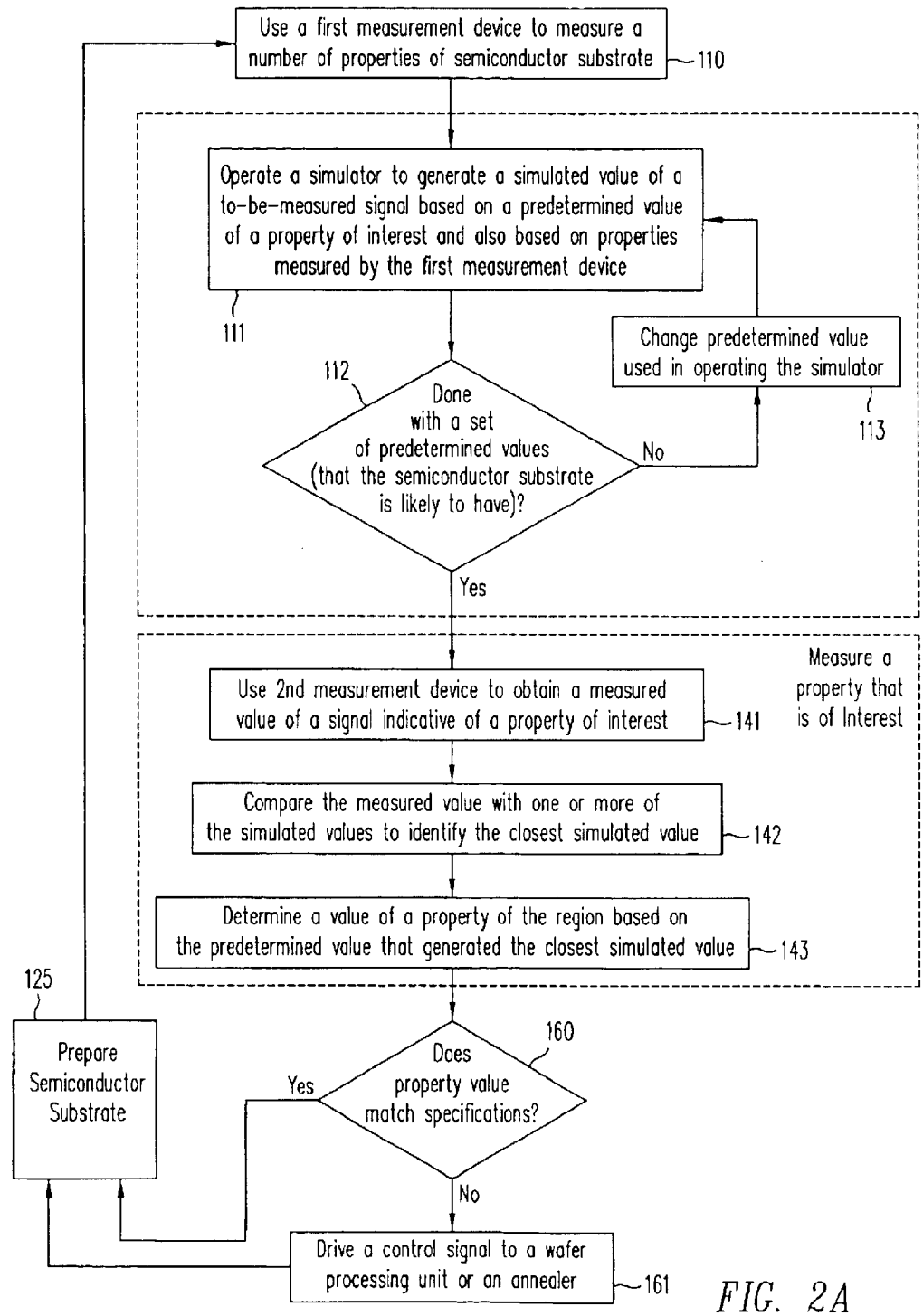
FIGS. 2A and 2B illustrate, in flow charts, two alternative embodiments of the method of FIG. 1A.

As noted above, in one embodiment, a property of a semiconductor substrate is measured by system 100 (FIG. 1B) as described herein. Specifically, system 100 uses a first measurement device 103A to measure (see act 110 in FIG. 2A) a number of properties of the semiconductor substrate. Next, system 100 uses (see act 111 in FIG. 2A) a simulator 103C to generate a simulated value of a to-be-measured signal, based on a predetermined value of the property of interest (e.g. a value identified in the specification), and also based on values of properties (other than the property of interest) that can affect the to-be-measured signal. The values of properties (other than the property of interest) are measured by the first measurement device 103A, for use by the simulator. In this embodiment, the simulator is repeatedly operated (see a loop formed by acts 112, 113 and 111), so that a number of simulated values are generated for a corresponding number of predetermined values (which may be selected to cover a range of values for the property of interest permitted by the specification).

Next, system 100 uses (see act 141 in FIG. 2A) a second measurement device 103B (FIG. 1B) to obtain a measured value of a signal indicative of the property of interest. Next, in one implementation, programmed computer 103C compares the measured value (see act 142 in FIG. 2A) with one or more simulated values (which may be held in, for example, a table) to identify the closest simulated value. Thereafter, programmed computer 103C determines (see act 143 in FIG. 2A) the value of the property of interest, based on a predetermined value for the property of interest that generated the closest simulated value.

For example, if the measured value is same as one of the simulated values, then computer 103C determines the property value to be the corresponding predetermined value. If the measured value differs from the simulated value by a certain percentage then computer 103C determines the property value of the semiconductor substrate to have the same percentage difference relative to the corresponding predetermined property value i.e. performs an interpolation.

Thereafter, computer 103C checks if the property value matches the specifications (see act 160 in FIG. 2A), and if so, the semiconductor substrate is processed further. If the property value does not match the specifications, computer 103C drives a control signal to, for example, layer formation apparatus 101 F on line 107 and/or to chemical mechanical polisher 102 on line 108, for process control. Note that even when a property value matches the specifications, if the property value falls within a predetermined range, process control may be performed (although the semiconductor substrate is not discarded) e.g. to correct an upcoming problem.

The just-described interpolation may be linear or nonlinear, depending on the embodiment (e.g. depending on the dependence of the property of interest on the signal being measured). Instead of using simulated values directly, computer 103C may determine a curve to which the simulated values fit, and then use the curve to look up the property value.

Figure 2B:
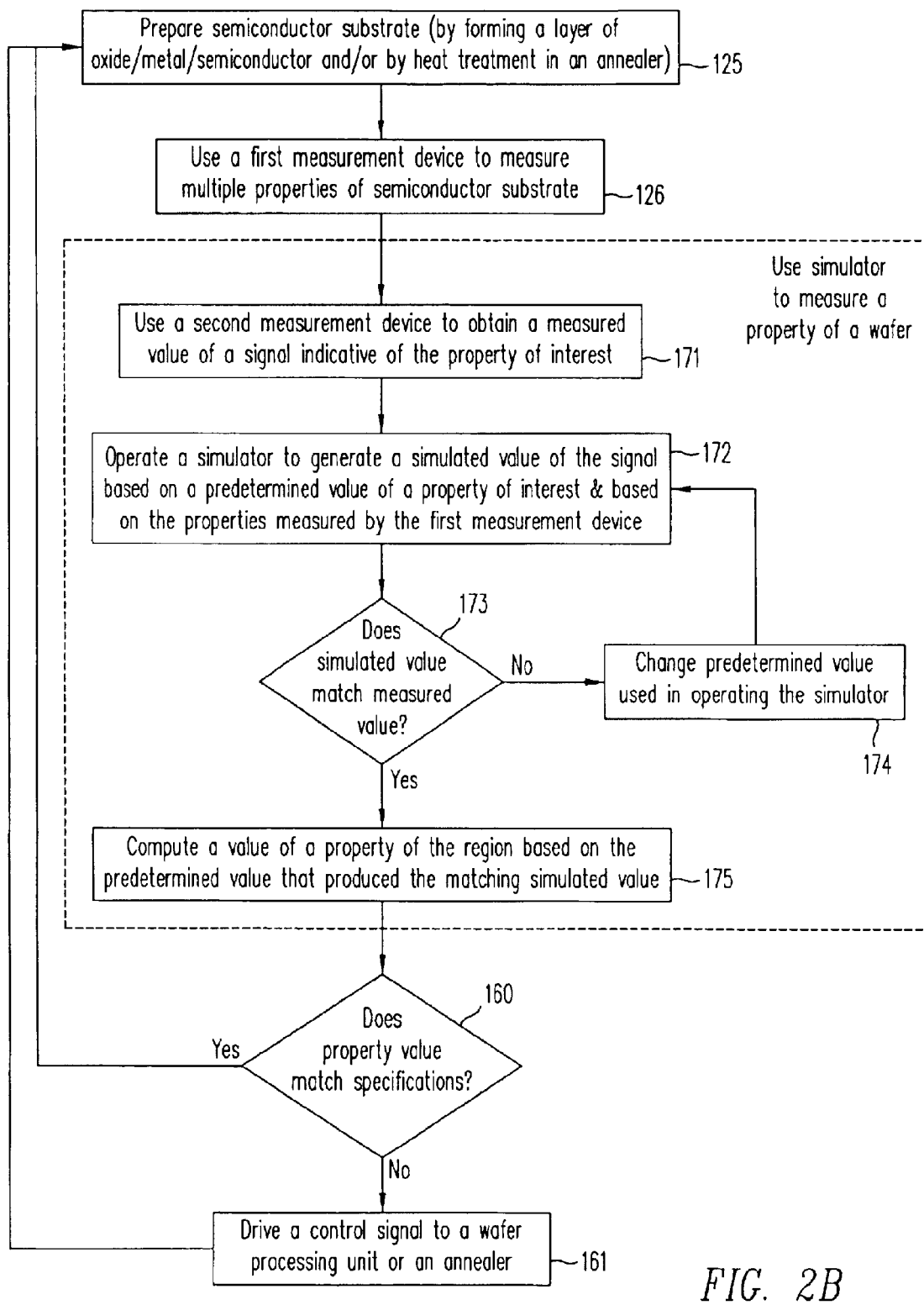

An alternative embodiment includes use of a look-up table based on externally generated values by another computer (when computation time is long) or based on empirical values or fits to empirical values. In another embodiment illustrated in FIG. 2B, the above-described simulation is not automatically repeated (in the loop formed by acts 112, 113 and 111), and instead, a measured signal from the second process (see act 171 in FIG. 2B) is compared (see act 173 in FIG. 2B) with a simulated value generated by the simulator (see act 172 in FIG. 2B), which is based on a predetermined value for the property as defined by the specification. If there is no match, the simulator is operated again, with another predetermined value of the property of interest (see act 174 in FIG. 2B), until a match is found. If there is a match, a value of the property of the region is computed (see act 175 in FIG. 2B), based on the predetermined value that produced the matching simulated value.

Figure 3A:
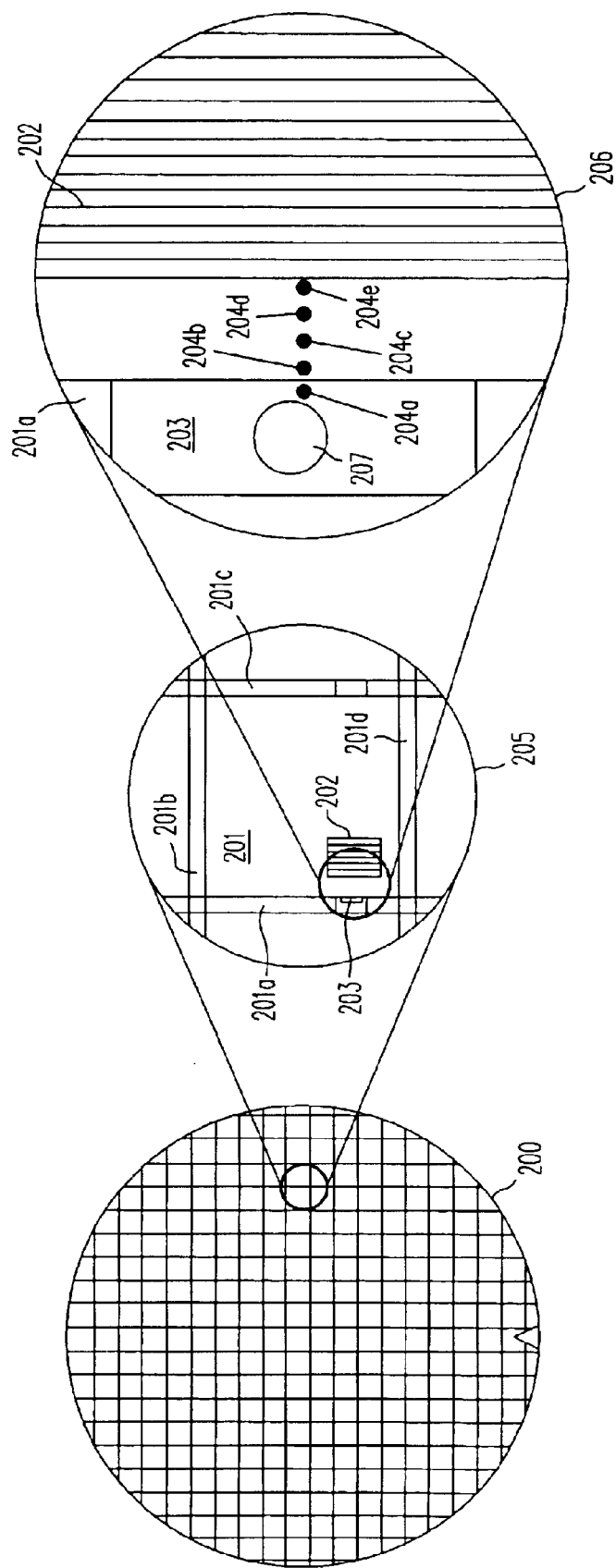
FIG. 3A illustrates locations on a patterned wafer at which measurements of the type illustrated in FIGS. 2A and 2B are made.

In one implementation, first and second measurements are performed at different locations: the first measurement in a test area, and the second measurement in an area of interest (such as a region containing a number of metal lines) of a wafer 200 (FIG. 3A) that is under fabrication. As noted above, such a workpiece may be a wafer having a number of areas (also called "die areas") that eventually form dice, such as area 201 shown in a circle 205 that is an enlarged view of a corresponding circle on wafer 200 (FIG. 3A). As illustrated in FIG. 3A, area 201 is surrounded by streets 201a–201d. Each of streets 201a–201d is, for example, 100 μm wide, and forms the area in which a saw is to be run, to separate the wafer into individual dies after fabrication is complete. Various areas in streets 201a–201d may be used for test patterns because such areas are better controlled than die areas in which integrated circuits are formed.

In this implementation, test area 203 (present inside circle 206 which is an enlarged view of a portion of wafer 200 illustrated in circle 205 in FIG. 3A) is chosen to be a box that is devoid of patterning, and is located in street 201a. Test area 203 is chosen to be within the nearest street to the area of interest (e.g. line array 202). Note that any other test area may be selected, e.g. if properties of the test area are well controlled, and if the area is arbitrarily near to (and preferably but not necessarily separated from) the area of interest. The properties that must be well controlled and that are measured in test area 203 are all of the properties that affect a measurement in the area of interest. In one embodiment it is assumed that these properties remain the same for both areas (i.e. the test area and the area of interest).

Figure 3B:
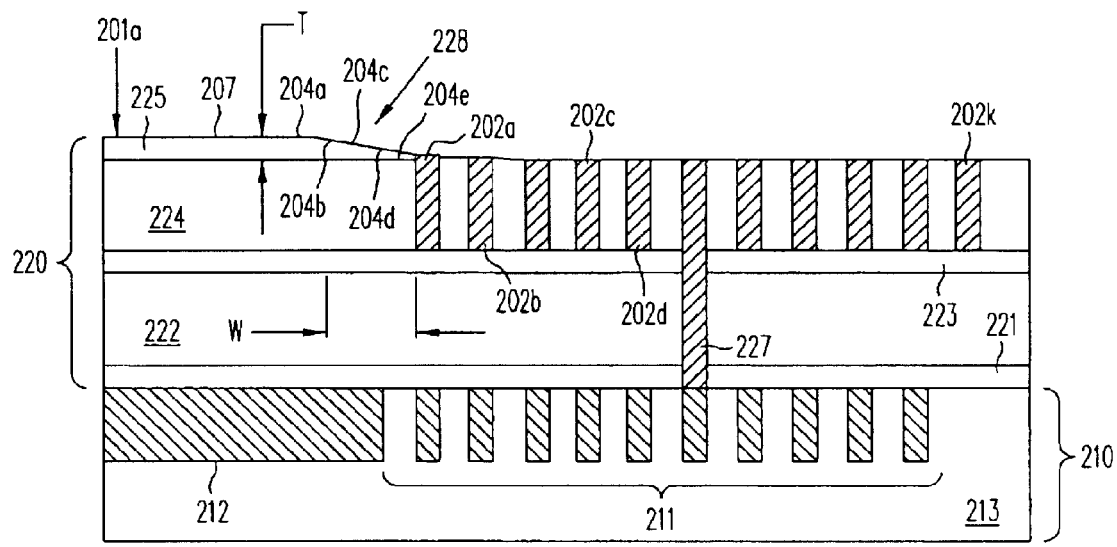
FIG. 3B illustrates a cross-section of a two level damascene structure in the patterned wafer of FIG. 3A, showing measurement locations.
Figure 3C:
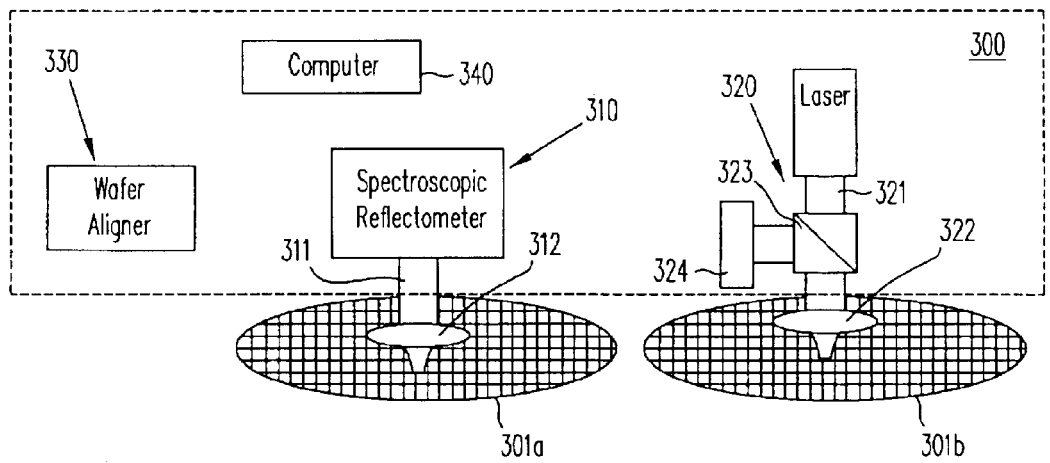
FIG. 3C illustrates one embodiment of the apparatus of FIG. 1B used with the patterned wafer of FIGS. 3B and 3C.

A first measurement may be made in a region 207 (e.g. of diameter 50 μm (in the example, the street is 100 μm, so the test area must be smaller)) in test pattern 203 (see FIG. 3A), which is located in a field region 201a as illustrated in FIG. 3B. If a destructive process (such as Secondary Ion Mass Spectrometry, or SIMS) is used to perform the first measurement, a pit is formed therein at the end of measurement. Moreover, one or more second measurements may be made at locations 204a–204e (FIG. 3A) that are between test pattern 203 and conductive lines 202. Lines 202 are embedded within a damascene structure (see FIG. 3B) that is formed in wafer 200, e.g. by chemical mechanical polishing.

Specifically, in one example, wafer 200 has a new level of metal interconnect formed (e.g. by apparatus 101 and polisher 102) over a preexisting structure 210 which is an underlying level of metal interconnect. Structure 210 includes a dielectric matrix 213, inlaid metal lines 211, and a pad (a large area feature) 212. Structure 220 has a dielectric stack and a set of inlaid lines. The dielectric stack may include etch stop layers 221 and 223, dielectric layers 222 and 224, and anti-reflection coating layer 225. The inlaid lines 202a–202K are formed in dielectric layer 224 and one or more via interconnects, such as structure 227, are used to connect the conductors in structure 220 to the conductors in structure 210. The function of etch stop layers 221 and 223 is to provide a material to stop the groove etching used to form the grooves in which lines 202a–202k are formed, and in which via interconnect 227 is formed. The function of the anti-reflection coating layer 225 is to control the optical properties of the stack for photolithography exposure.

Structures 210 and 220 of wafer 200 (FIG. 3B) may be fabricated in any manner well known in the art. In one example, structure 220 is formed in the following manner. First, on structure 210, a dielectric stack of layers 221–225 (FIG. 3B) is formed. Thereafter, grooves are etched through layers 225 and 224, stopping at layer 223. Next, layer 223 is removed at the point where via interconnect 227 is to be formed. Thereafter, a hole is etched for via interconnect 227 through layer 222, stopping at layer 221. Next, layer 221 is removed at the bottom of the hole, exposing the metal line in structure 210. Thereafter, the grooves are filled with metal such as copper. Such filling leaves copper over the top of the entire structure. The resulting structure is polished by polisher 102 (FIG. 1B), removing the blanket copper film coating the top of structure 220 and leaving lines 202a–202k remaining, thereby to form structure 220.

In addition to removing the excess copper, polisher 102 may also remove some dielectric material over lines 202a–202k, so that layer 225 in structure 200 becomes increasingly thin when going from street 201a towards a first conductive line 202a (FIGS. 3B and 3A), i.e. layer 225 has the shape of a wedge when viewed in cross-section. The slope (which is thickness T of the sloping surface divided by width W of layer 225) can be small as compared to other slopes e.g. width W may be 10 μm (100,000 Å) and thickness T may be 200 Å, so slope is $\frac{1}{500}$, or about 0.12 degrees. However, the slope can be much larger if polisher 102 is not well controlled. The sloped region 228 (also called "erosion edge") may occur within 10 μm of metal lines 202a–202k. Such an erosion edge 228 may also extend into line array 202.

The slope of an erosion edge of wafer 200 can be measured with high depth resolution (e.g. 10 Å) and spatial resolution (e.g. 1 μm) based on multiple measurements of the type described herein. Specifically, wafer 200 is loaded by an aligner 330 onto a stage (not shown) and moved under system 300. In this example, wafer 200 has a two layer coating consisting of an anti-reflection coating (ARC) 225 (e.g. of thickness 603 A) over silicon dioxide layer 224 (e.g. of thickness 3479 A). In one example, there are actually 5 dielectric layers over the reflecting surface of pad 212: ARC layer 225, silicon dioxide layers 222 and 224, and etch-stop layers 221 and 223. The index of refraction and thickness of these layers are measured over pad 212 in the reference measurement. Wafer 200 is placed in system 300 and aligned by aligner 330 so that a measurement by a first measurement device 310 is done in test pattern 203 (FIG. 3A).

Specifically, system 300 has two measurement devices 310 and 320, with a site to be measured in wafer 200 located at position 301a under the first measurement device 310 and after the measurement is completed the same site in the same wafer 200 is located (by wafer aligner 330) at position 301b under the second measurement device 320.

First measurement device 310 includes a broadband spectroscopic reflectometer well known in the art. Such systems consist of a white light source that creates optical beam 311, which is focused onto wafer 200 at position 301a with lens 312. The numerical aperture of lens 312 may be, for example, 0.2 and the spot size may be on the order of, e.g. 20 µm. Such a spectroscopic reflectometer is available commercially from, for example, Ocean Optics of Dunedin, Fla.

Optical beam 311 is of white light (also called "polychromatic white light"), and includes light from multiple parts of the color spectrum (e.g. the presence of multiple colors), such as the light produced by an incandescent bulb or a halogen lamp. Such white light typically covers a spectral range of 300 to 800 nm. Measurements of reflection are taken at 40–80 equally spaced wavelengths over the full spectral range using the spectroscopic reflectometer 310.

White light is used in first measurement device 310 so that multiple parameters (e.g. refractive index and thickness of each of four layers in a stack) may be measured by sensing reflectivity of light at a large number of different wavelengths (e.g. at wavelength starting at 300 nm and incrementing by 10 nm until 800 nm), in the normal manner of a spectrometer. As noted above, such measurements are used by a computer 340 to generate a function to be used with a measurement from the second measurement device 320 to determine a value of the property of interest.

In this particular embodiment, computer 340 is programmed with analysis software to take the reflection vs. wavelength signal from measurement device 310 and convert the signal into a table of thickness and index of refraction of each layer. Such software is available commercially, for example, as WVASE32 Analysis software sold by J. A. Woollam Company, Inc. of Lincoln, Neb., and is described in the user's manual entitled "Guide to Using WVASE32," 1995, available from J. A. Woollam Company, Inc. Instead of WVASE32 Analysis software any other ellipsometric analysis program may be used.

Figure 4:
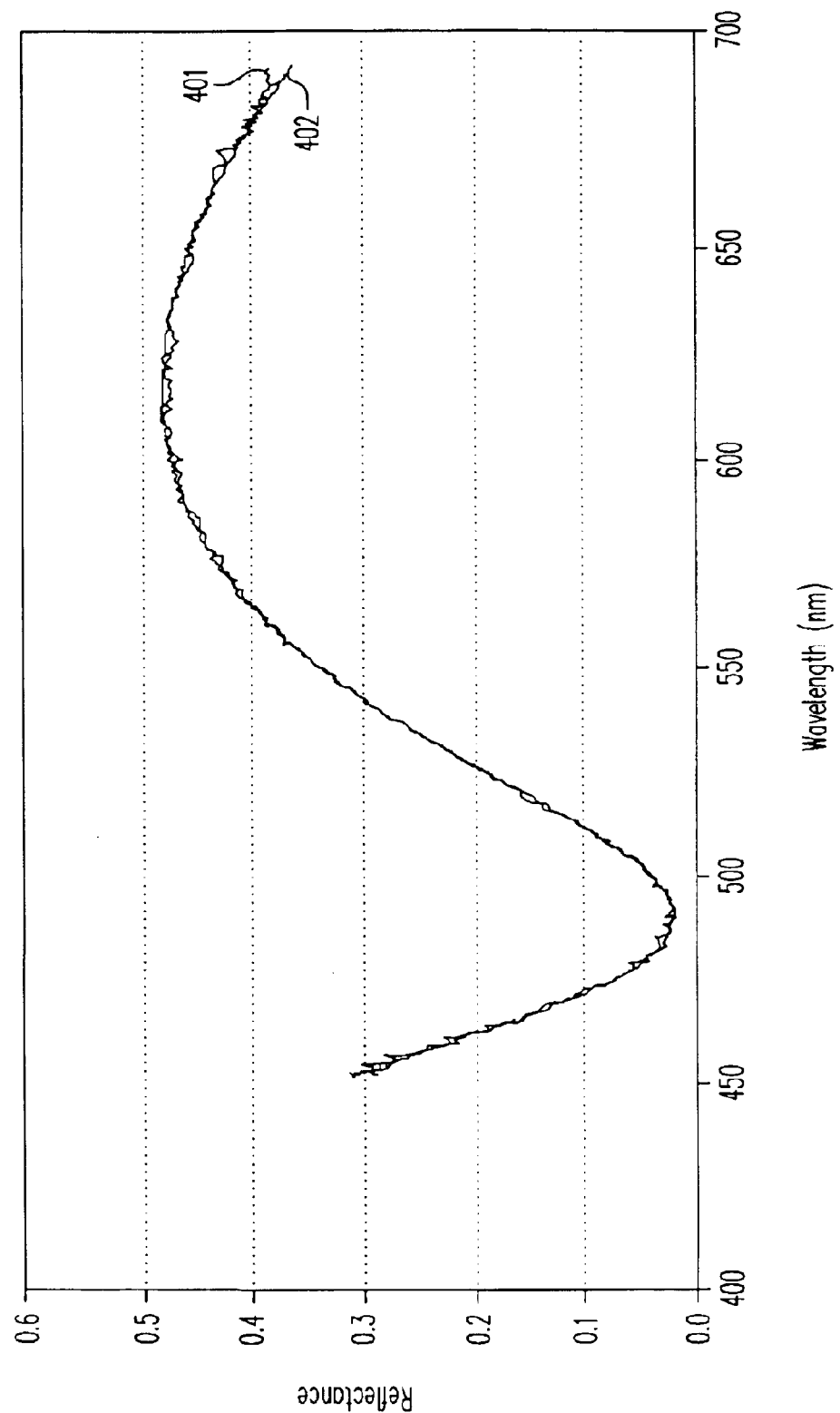
FIG. 4 illustrates fitting measurements from a single measurement device of the apparatus of FIG. 3C to a curve, to obtain thickness and refractive index values of two layers (namely an antireflective coating on an oxide coating) in one example.

When programmed with such software, computer 340 employs curve fitting methods to fit measurements 401 to a curve 402 (see FIG. 4). In one example, computer 340 is informed of the number of layers that are present in wafer 200 (based on the fabrication process), and is also informed of nominal values for thicknesses of the layers, the materials used to form the individual layers and the position of the layers relative to one another. For example, for wafer 200 illustrated in FIG. 3B computer 340 is provided with information in the following table.

In this example, computer 340 uses such information as an initial model for wafer 200, and uses look-up tables supplied with the software, for the index of refraction of the ARC and silicon dioxide layers, to determine any changes to be made to the initial model. Specifically, computer 340 varies the index of refraction and thickness of each of the layers until a model is found that generates a good fit for the experimentally measured reflectance across the electromagnetic spectrum. In FIG. 4, curve 402 is the best fit for measurements 401. After such calibration, computer 340 determines that in spot 207 the thickness of the ARC layer 225 is 603 Å and the thickness of the silicon dioxide layer 224 is 3479 Å.

Figure 5:
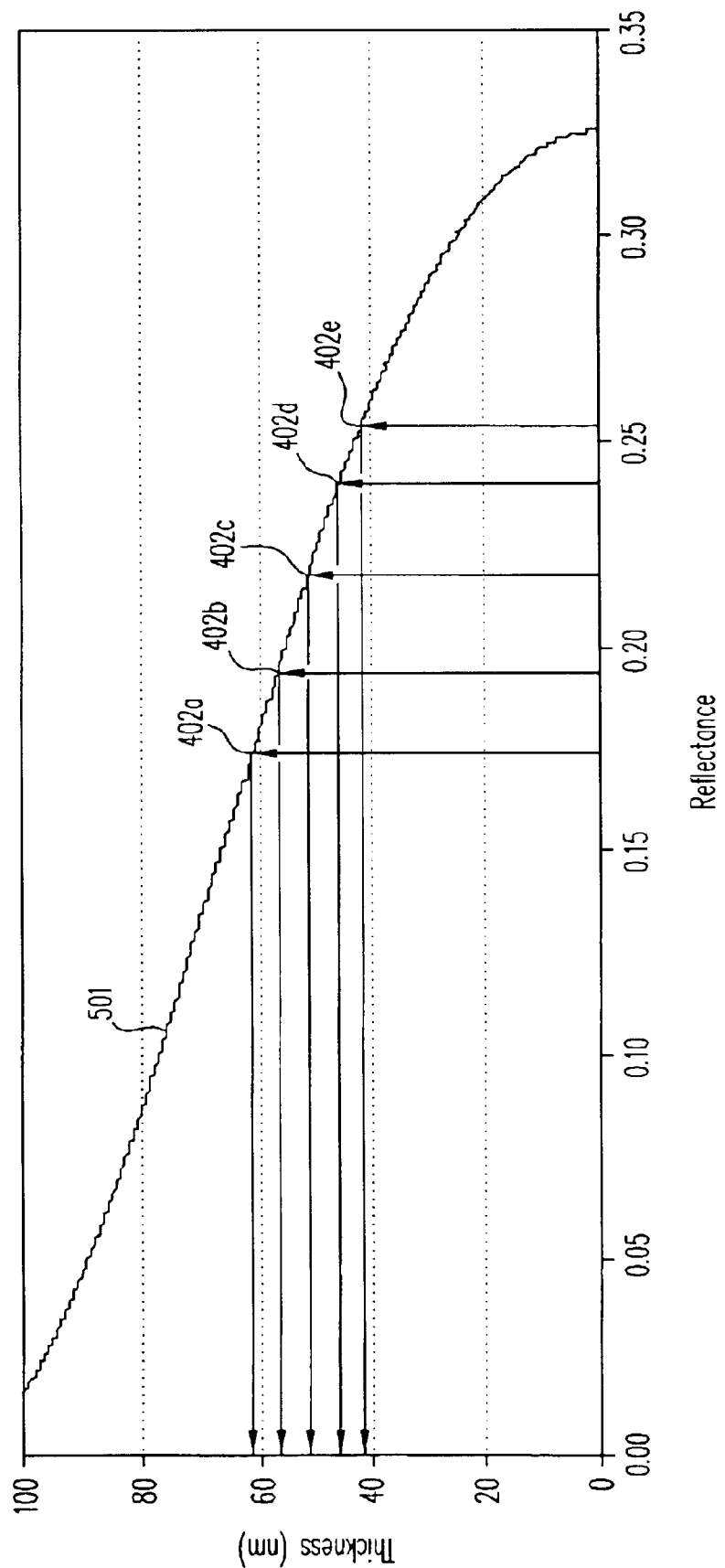
FIG. 5 illustrates a model of thickness of an uppermost layer as a function of reflectance, and use of the model to determine actual thickness using a single-wavelength (e.g. 830 nm) measurement of reflectance.

In addition to generating a model of wafer 200 based on measurements from first measurement device 310, computer 340 in accordance with the invention also uses the model to generate reflectance and/or transmission data for the uppermost layer 225 (FIG. 3B). Specifically, a reflectance generation function of computer 340 is used to determine reflectance of wafer 200 as a function of thickness of the uppermost layer 225, at the frequency (e.g. 830 nm) of a laser beam 321 used in second measurement device 320 (discussed below). This function is illustrated in FIG. 5, by curve 501.

Note that a laser beam 321 is used in a second measurement device 320, and therefore the laser beam itself is not used in the first measurement device 310. Moreover, although a sensor at the wavelength (e.g. 830 nm) of laser beam 321 may have been used during the first measurement, this is not necessary. In the example illustrated in FIGS. 4 and 5, there may not be sampling of reflectivity at the specific laser wavelength (e.g. if the laser wavelength is 827 nm), and instead the function represented by curve 501 is determined from the model which is constructed from measurements by device 310.

Depending on the embodiment, at the time computer 340 generates the reflectance and/or transmission data for layer 225, laser beam 321 may or may not have been applied to wafer 200. So, variation of a material property (in this example thickness) as a function of a to-be-measured signal (in this example reflectance) is determined from the measurements by device 310. When plotted on a graph, this function is also called "calibration curve", and is illustrated in FIG. 5 by curve 501.

Second measurement device 320 of this embodiment includes a laser reflectometer that produces a collimated laser beam 321. Lens 322 focuses beam 321 onto a site (e.g. of diameter 1 µm) on wafer 200 when located at position 301b. The reflected laser light is sent to detector 324 with beam splitter 323. Detector 324 provides a measurement, which is used as described above, with a function obtained from simulation (represented by curve 501 in FIG. 5), to look up a value of the property of interest.

Depending on the embodiment, more than one laser beam may be used by device 320 to illuminate the same site, e.g. two monochromatic songs may be modulated at two corresponding frequencies and light reflected by the site filtered at these frequencies obtain reflectances of the site at the respective wavelength of the two sources.

In one embodiment, the slope of erosion edge 228 (FIG. 3B) is measured by scanning wafer 200 under the spot of a beam 321 in small increments, say 1 µm steps towards array 202 (FIG. 3A), and a measurement is taken after each step. For example, five measurements are made at the corresponding locations 204a–204e, spaced 2.5 µm apart, providing reflectance values 402a–402e. The first value 402a yields a thickness of 603 Å for layer 225, which is consistent with the measurement in test pattern 203. Note that the first location 204a may be at a point prior to the erosion edge, so that the thickness of ARC layer 225 is the same as for the reference measurement. The value of the ARC thickness at this point may be used to verify that the first and second measurements are properly calibrated.

Figure 6:
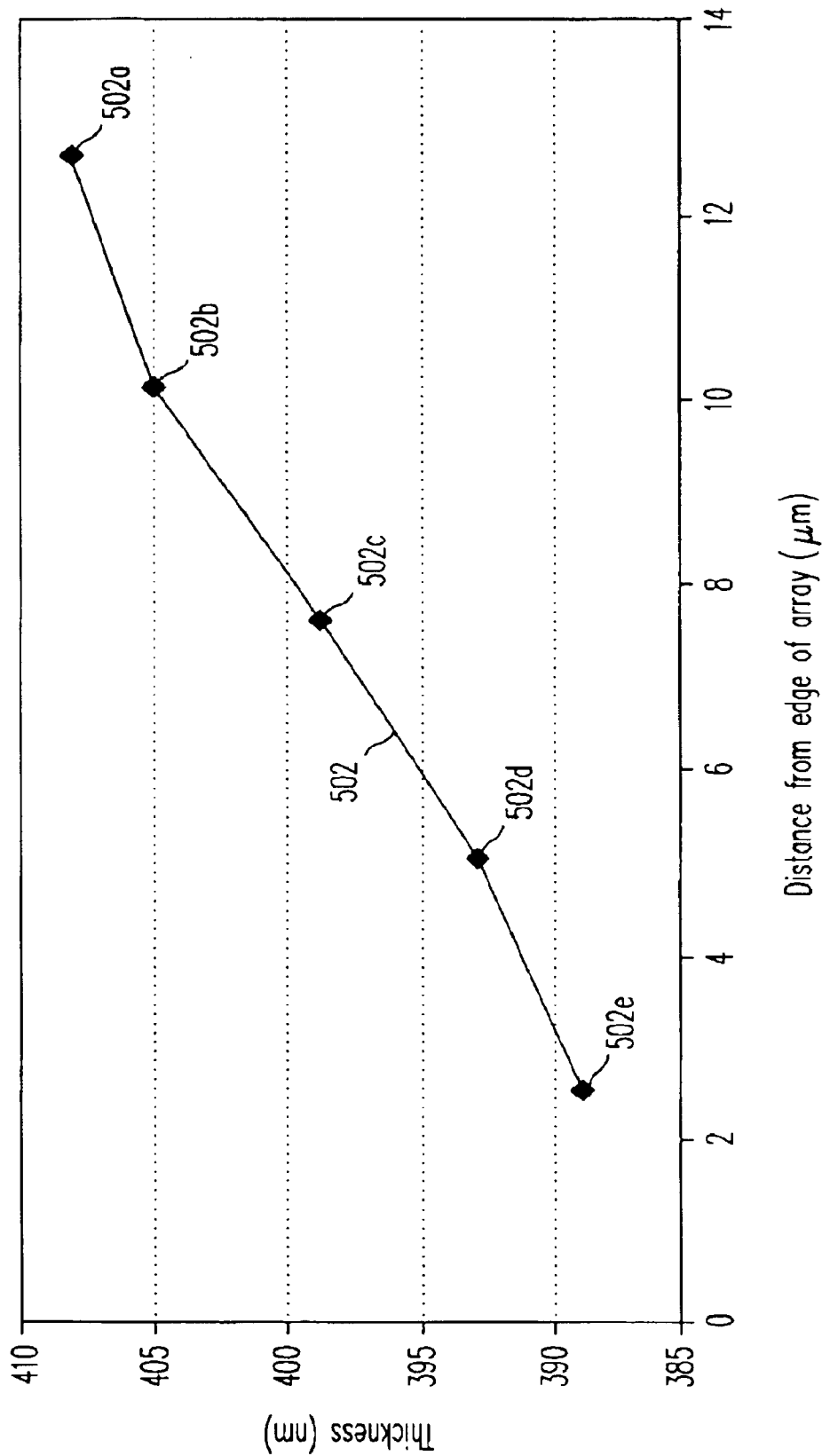
FIG. 6 illustrates a graph of dielectric thickness (including the antireflective coating and the oxide coating) as a function of distance from a line array measured in one example.

Progressive measurements 204b–204e map the erosion edge 228. In the above-described example, the thickness of the silicon dioxide layer 224 is added to the measured thickness of the antireflective coating 225, to obtain total thickness of the stack. The data points are then plotted as points 502a–502e (FIG. 6) corresponding to measurement points 402a–402e, thereby to yield a line 502. Line 502 provides a graph of the thickness as a function of distance from the left edge of array 202.

Use of first measurement device 310 during fabrication of a wafer as described herein, calibrates a laser reflectometer for each wafer being evaluated. Combination of the measurements from devices 310 and 320 as described above assumes that initially all thickness variation is due solely to a diminishing thickness of the topmost layer, for example, anti-reflection coating 225. When the measured thickness change becomes greater than the thickness of anti-reflection coating 225, computer 340 assumes that the thickness change comes solely from a diminishing thickness of the uppermost layer which is the next layer in the stack, for example, dielectric layer 224. In this manner, computer 340 of this embodiment always determines only one parameter—the thickness of the uppermost layer—using one measurement—reflectance at a single laser wavelength.

In some cases, a laser at a second wavelength (which is different from the first wavelength) may be used to make an additional measurement in device 320, and computer 340 uses the additional measurement instead of the measurement at the first wavelength, because the reflection signal is periodic in thickness, so that certain thickness values may be at a maximum or minimum where the derivative with respect to thickness is zero (thereby leading to ambiguity). In such cases the measurement at the first wavelength provides less resolution than the additional measurement at the second wavelength.

Figure 3D:
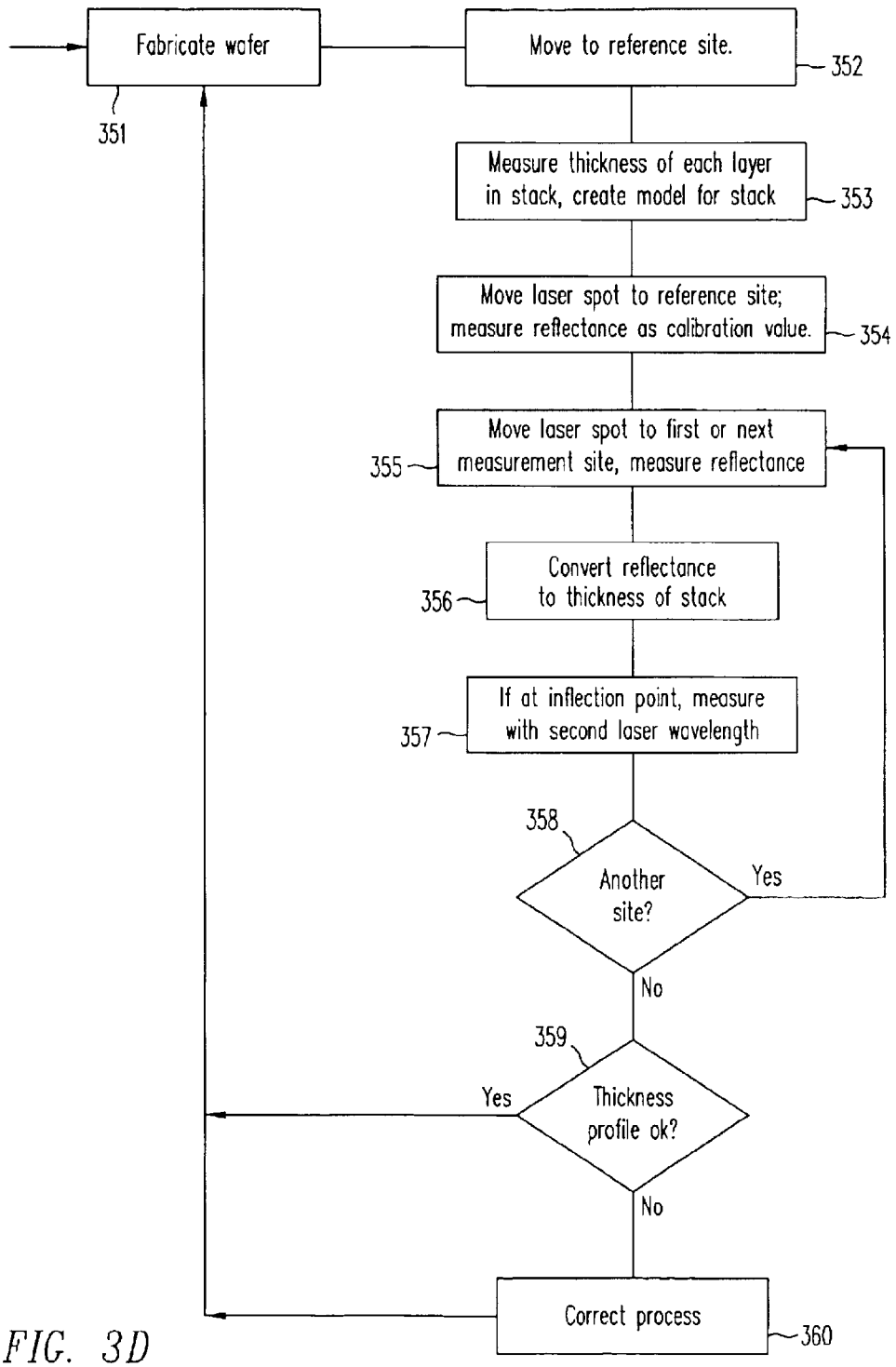
FIG. 3D illustrates, in a flow chart, process control using the apparatus of FIG. 3C.

FIG. 3D illustrates a decision flow chart associated with measurement of a property of interest in one particular implementation of the invention. In step 351 a wafer 200 is loaded into the measurement system 300. In step 352 wafer 200 is moved to a position so that in step 353 the spectroscopic reflectometer can measure the thickness of each layer in the stack at a location near the site of the high-resolution measurement and create a model for reflectance at the wavelength (e.g. 830 nm) of a laser in the laser reflectometer. In step 354 the reference site is moved under the high-resolution laser spot and the reflectance is measured. This provides a reference model to be used in calibrating the reflectance signal measured at the laser wavelength.

A loop of steps 355–358 is now entered where measurements are performed at a series of sites, for instance as a line scan with points spaced by a fixed distance to scan over an erosion edge. In step 355 the system moves to a measurement site, a focus is performed, and the reflectance is measured. The reflectance is then converted to thickness of the top layer and, by adding the thickness of the underlying layers, the thickness of the stack is found in step 356.

If thickness measurement based on the current model for stack 220 indicates the entire topmost layer is removed, a second model is created (e.g. by omitting layer 225 from the current model), and used to measure the thickness of the next layer 224 (which is now the uppermost layer) assuming the absence of layer 225. In step 357 (FIG. 3D) the data is optionally further analyzed (although, in the simplest form, the thickness is reported and the measurement process is done).

If the reflectance vs. thickness curve is near an inflection point in a model the thickness resolution is poor, (i.e. the resolution is less the process tolerance; for example, if the process can tolerate ±50 Å and the resolution is 50 Å, then the resolution is poor; a stricter definition is based on 3 standard deviations, so the resolution must be 3 times the tolerance), and in such an event a second measurement may be made with a second laser at a second wavelength to obtain a higher resolution thickness measurement. Finally, in step 358 (FIG. 3D) a decision is made as to whether all sites have been measured and the scan is complete, or whether the next site should be measured.

After the measurements are complete, the thickness profile is analyzed in step 359 to determine, for example, if the erosion step is too deep. Examples of erosion values could be from 100 to 1000 Å. Too deep is a matter of process tolerance, but values on the order of 1000 Å may be considered unacceptable. If the profile is ok (either it matches a profile that is obtained on devices that perform properly, or the erosion depth is within tolerance, as determined by the process) the loop is complete and a new wafer is measured, or a new site on the same wafer is measured. If the profile is not ok, in step 360 the fabrication process is corrected before measuring the next wafer.

Sometimes it is desired to make a single measurement rather than a scan over a region. The advantage of a scan is that the dielectric stack structure at the starting point in the second measurement device 320 is equal to the stack as measured by the first measurement device 310. The top layer 225 then diminishes in thickness from that point. As noted above, at some point, the top layer 225 may be fully removed, and a second model of the stack that does not incorporate the original top layer is used.

If device 320 is to measure only at a specific location of interest (also called "measurement site") instead of the above-described scan, it may be ambiguous from such a measurement as to whether the topmost layer in the region measured by device 310 is or is not present. In this case, an alternate procedure described next is followed using two lasers at the specific location of interest, and the lasers have two different wavelengths $\lambda 1$ and $\lambda 2$.

1. A number of reflectance measurements at a corresponding number of wavelengths are made by device 310, to determine the optical constants and thicknesses of the layers in the stack in test pattern 203 (also called "reference site") in the manner described above.
2. Computer 340 is programmed to create a number of models that predict thickness as a function of reflectance measured by device 320, for four cases: namely for each of two wavelengths $\lambda 1$ and $\lambda 2$ and with and without the topmost layer in test pattern 203.
3. Two reflectance measurements are made by device 320 at the reference site to calibrate the reflectance of lasers with wavelength $\lambda 1$ and $\lambda 2$.
4. Two additional reflectance measurements are made at the measurement site at wavelengths $\lambda 1$ and $\lambda 2$.
5. Computer 340 is programmed to determine thickness for the four cases (two wavelengths, with and without the topmost layer)
6. Computer 340 is further programmed to compare thickness values for the two wavelengths $\lambda 1$ and $\lambda 2$, for each of two cases (with and without the topmost layer). Computer 340 is also programmed to select the case where the thickness values most closely match, as the correct case.

In one example, a first model including the topmost layer gives a thickness of 985 nm for $\lambda 1$ and 755 nm for $\lambda 2$, and a second model without the topmost layer gives a thickness of 694 nm for $\lambda 1$ and 696 nm for $\lambda 2$. The difference for the case of a topmost layer being present is 230 nm and the difference for the case of the topmost layer being removed is 2 nm. On comparison of the two differences, the 2 nm difference is smaller than the 230 nm difference, and therefore the case of the topmost layer being removed is selected as the correct case, and the second model is used to determine the property of interest. In this example, computer 340 determines that the thickness is an average of the two readings, i.e. 695 nm.

Figure 7:
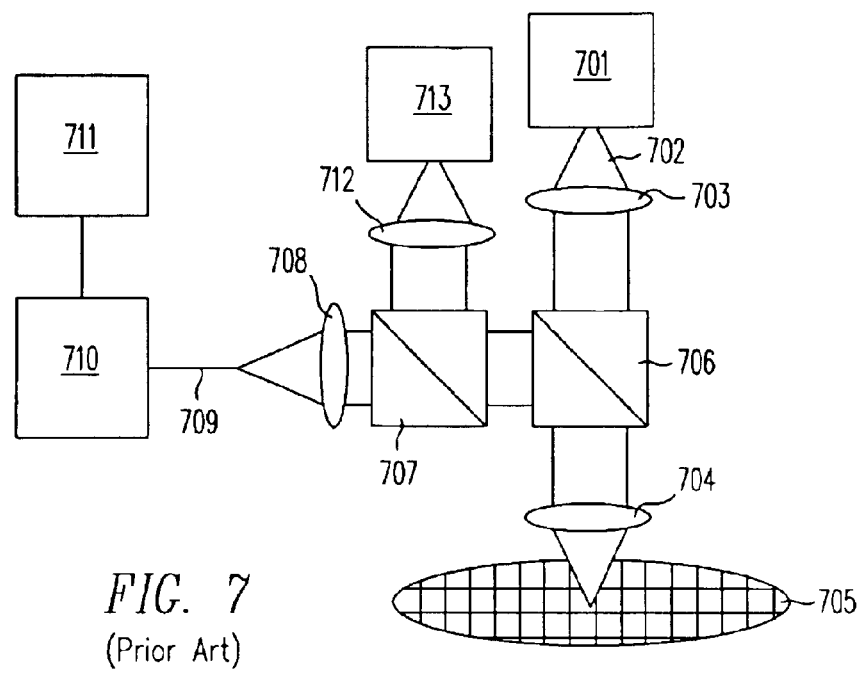
FIG. 7 illustrates, in a detailed block diagram, a spectroscopic reflectometer of the prior art, which is used as item 310 in the apparatus of FIG. 3C.

FIG. 7 shows a schematic of the reflectometer apparatus, which provides the low resolution characterization of the multiple-film stack. Note that the apparatus of FIG. 7 is not a new invention by itself, and is constructed with commercially available components. White light source 701 emits light 702 that is collimated with collection optics 703 to form a beam of white light that is nearly focused on the wafer 705 with objective lens 704 (a near focus point is used to prevent imaging the lamp filaments, thereby providing uniform illumination in the spot).

Specifically, lens 704 collects light reflected from wafer 705. The reflected light is diverted using beam splitter 706. The reflected light passes through beam splitter 707 and is focused into fiber 709 with lens 708. Fiber 709 couples the reflected light to spectrometer 710 (Ocean Optics), which provides an output signal giving the reflection as a function of wavelength. The reflection vs. wavelength data is sent to computer 711.

In one implementation, computer 711 is programmed with WVASE32 Analysis software (available from J. A. Woollam Company, Inc. Lincoln, Neb.) that includes dispersion models (models of index of refraction vs. wavelength) for the materials in the stack and determines the thickness of each layer by optimizing the fit between a model and the measured data. The WVASE32 Analysis software also calculates a table of thickness of the top-most layer as a function of reflectivity at the measurement laser wavelength. A similar table may also be calculated in the absence of the top layer for cases where the top layer has been completely removed and the erosion step 28 occurs in the layer underneath the top layer.

Beam splitter 707 diverts a portion of the reflected beam to a low-power vision system used to find the measurement site on the wafer 705. This consists of a microscope formed by the combination of objective lens 704 and lens 712. Video camera 713 provides an image to a pattern recognition system (Cognex Corp.) to perform site alignment.

Figure 8:
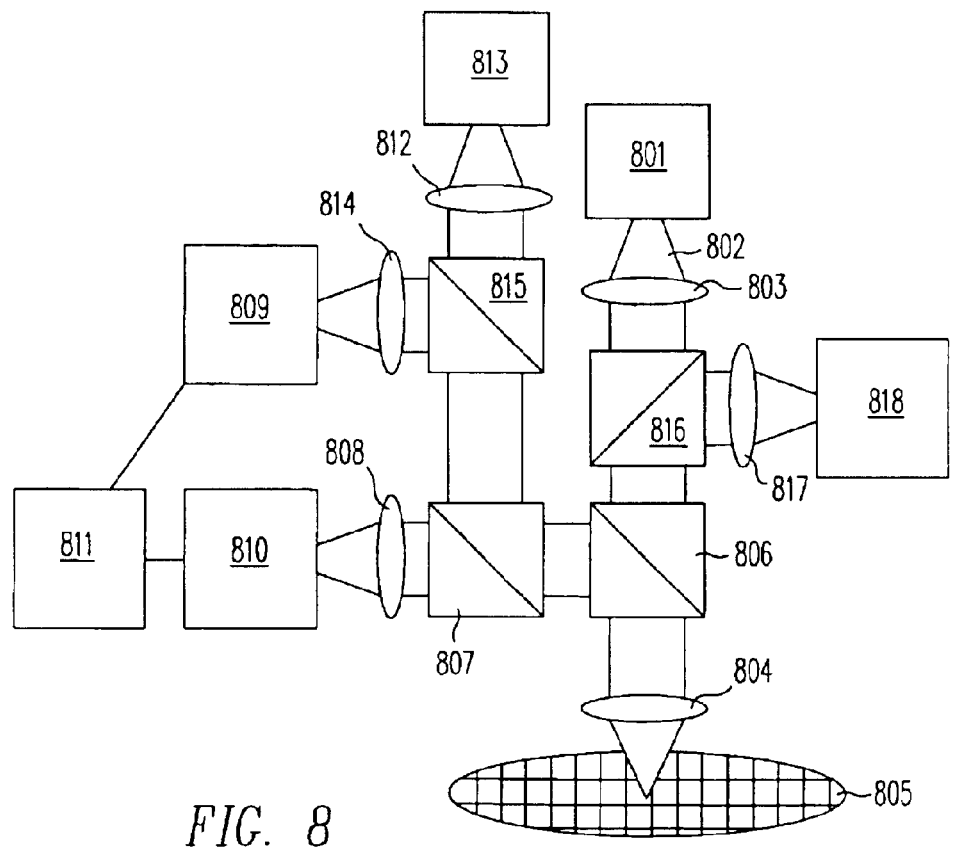
FIG. 8 illustrates, in a detailed block diagram, a laser reflectometer of the prior art which is used as item 300 in the apparatus of FIG. 3C.

FIG. 8 shows a schematic of the laser reflectometer hardware, providing a high resolution measurement. Laser 801 (830 nm laser with 100 mW emitted power from Spectra Diode Labs of San Jose, Calif., for example) emits beam 802 that is collimated using lens 803 to a beam diameter of 2.3 mm. Beam 802 is then focused on a site on wafer 805 with objective lens 804, which is a 100×, NA=0.9 lens from Olympus of Tokyo, Japan. The spot size is about 1 $\mu$m at the surface of wafer 805.

Before a measurement is taken, the wafer is moved to the measurement site and focused. Movement to the measurement site is accomplished by illuminating the sample with white light for the purpose of imaging. The white light source 818 is collimated with lens 817 and is injected using beam splitter 816. The reflected white light is imaged with a microscope formed with the combination of lens 804, beam splitter 815, and lens 814. Camera 809 images the site and the wafer is aligned according to stage motions initiated by the pattern recognition software that runs in computer 811. During the site alignment laser 801 may be turned off or shuttered to prevent the bright laser light from swamping camera 809. Alternately, the laser power may be turned to a minimum value so the laser spot may be viewed overlaid on the wafer pattern to confirm the exact site of measurement.

The focus at the site is then accomplished using the auto-focus consisting of lens 812 and auto-focus, element 813 including a pinhole and a detector. Laser 801 is used as the light source for the auto-focus.

Following focus at the site, the reflectance is measured. Laser beam 802 is collimated with lens 803 and focused onto the wafer 805 with objective lens 804. The return reflection is split off with beam splitter 806, passes through beam splitter 807 and is focused onto detector 810 with lens 808. The signal is digitized and sent to computer 811, which compares the reflection to the model generated earlier to determine the thickness of the topmost layer according to the procedure previously described.

In the event that a second laser wavelength is desired (e.g. to eliminate ambiguity in depth measurement caused by an inflection point as discussed elsewhere herein), such a laser may be coupled into the system in FIG. 8 in a manner analogous to the white light source 818. In this case, the second laser beam is collimated and injected collinear with the beam from laser 801 using a beam splitter similar to element 816.

It may be necessary to calibrate the laser reflectance. This is done either by measurement on a reference sample of known reflectance, or by measurement at the site used with the low resolution reflectometer measurement. Alternately, the first measurement site of a scan may be chosen outside of the eroded area, and the thickness at this site may be assumed to correspond to the thickness measured with the low resolution reflectometer in the test pattern.

In one application of a measurement as described herein, a wafer requires a next level of metal interconnection. The wafer goes into process module 101 (FIG. 1B), where an interconnect layer is formed, including dielectric stack deposition, groove etching, backfill and polishing. The wafer, with the completed additional interconnect layer, is measured in system 103 that applies the high resolution dielectric measurement to determine that the polishing process has been successfully completed. Results of measurements performed by system 103 are transferred to computer 103C. In the event that results are judged unacceptable (for example, because erosion is too deep), signals are sent to process module 101 to alter or halt the process to enable correction of the problem.

As noted above, two or more lasers can be used to increase the accuracy of the measurement. In certain cases, the reflectance is cyclical with the thickness of the layer. For example, the reflection of a single layer is a cosine function of the wavelength. Therefore, there are certain values of thickness where the change in reflectance with respect to thickness is zero (where the argument of the cosine is 0 or $\pi$). At those thickness values, a second reading can be made with a second wavelength, where the change in reflectance with respect to thickness is non-zero. This increases accuracy across the full range of thickness values. Alternately, the second laser can be used instead of the first when the reference measurement indicates that the thickness lies at an inflection point of a model based on a measurement using the first laser.

If one or more lasers are used to make measurements as described herein, one or both lasers can be modulated for the reflectance measurement. This has various advantages. For example, a pumping laser may already be modulated, so it is simple to read the modulated reflectance of this laser alone by removing a blocking filter from the front of the detector. Also, measuring the reflectance of a modulated laser beam enables use of the lock-in amplifier to measure the reflectance signal. This provides a very accurate, noise-free measurement, much more accurate than available with a dc measurement.

In addition, if one laser is modulated and the other is not, the reflectance of both beams can be measured simultaneously by measuring the modulated laser reflectance with a lock-in amplifier and measuring the unmodulated laser reflectance with a dc amplifier. This increases throughput over measurement of dc reflectance of both beams, since the measurement of the dc reflectance of each beam must be done in sequence rather than in parallel.

The laser light can also be polarized to enable use of methods as described in U.S. patent application Ser. No. 09/521,232. For example, if the light is polarized with the electric field vector perpendicular to the direction of the metal lines, then the metal lines will be "invisible" (have a very small cross-section to the laser light). It is then possible to measure the dielectric thickness within the metal arrays.

Low resolution values can be used in case of dielectric measurements, in two ways. First, if the dielectric step to the array is measured, as with the above methods, then the dielectric thickness at the array edge is known. This value can be used to extend the high resolution measurement into the array. Second, a model could be built to measure dielectric thickness with low resolution in the array—this would be exactly analogous to the measurement in the test pattern, only a new model would be required, since the WVASE32 software will not handle measurement in an array.

Another embodiment for the high resolution measurement uses two high resolution lasers at the same time. This embodiment has a real advantage in that the reflectance at both wavelengths can be measured simultaneously, thereby speeding up the measurement. One high resolution laser is modulated at one frequency and the other at a second frequency, or one is modulated and the other is at constant power (dc). The detector signal is then split using either two bandpass filters or a high-pass and low-pass filter (the latter can be a capacitor to block dc and pass ac). The signals from both lasers are read at the same time.

For example, the 830 nm laser is modulated at 2 kHz and the 980 nm laser is operated at constant amplitude. Both beams are reflected from the sample and intercepted with the detector. The detector signal is capacitively coupled to a first amplifier, whose signal measures the reflection at 830 nm. The detector signal is also sent through a low-pass filter to a second amplifier, whose signal measures the reflection at 980 nm.

In another embodiment, the 830 nm laser is modulated at 2 kHz and the 980 nm laser is modulated at 0.2 kHz. The detector output is sent to two bandpass filters, one set at 2 kHz and the second at 0.2 kHz. The output of the first filter provides the reflectance signal at 830 nm; the output of the second provides the reflectance signal at 980 nm.

Numerous modifications and adaptations of the above-described embodiments, implementations, and examples will become apparent to a person skilled in the art of measuring properties of various workpieces in general and semiconductor wafers in particular. For example, in an alternative embodiment, instead of using a laser to make the high resolution measurement, measurement by another method (e.g. near-field optical microscopy) may be used.

In certain embodiments, the first measurement and the second measurement are performed in sequence (in any order), without any intervening process steps of wafer fabrication. In some implementations, a number of first measurements are made in sequence one after another before a corresponding number of second measurements are made. In other implementations, a pair of measurements (namely a first measurement and a second measurement) are made in sequence, followed by another pair of measurements. In another implementation, a first reference measurement is made and used as a common reference for a set of near-by high-resolution measurements.

In another embodiment, two or more measurements of the type described above are made employing the same process although the resolution of each measurement may be different, and the measurements are used together to determine the property of interest. For example, a low resolution measurement is used to calibrate a high resolution measurement.

Furthermore, acts of the type described herein can be combined with acts described in any of U.S. patent applications, Ser. Nos. 09/799,481, 09/544,280, 09/276,821, 09/521,232 and 09/788,273 incorporated by reference above.

Also, the above-described method 90 of FIG. 1A (which is performed when executing acts 10–70) can also be performed in a manner similar or identical to that described in the related U.S. patent application, Ser. No. 09/274,821, entitled "APPARATUS AND METHOD FOR DETERMINING THE ACTIVE DOPANT PROFILE IN A SEMICONDUCTOR WAFER," filed Mar. 22, 1999, by Peter G. Borden et al. (incorporated by reference above), with a production wafer used in all acts of the method. The dopant profile can be measured with a SIMS at a reference site (in this case, the reference site might be the center of the wafer because SIMS has very low throughput, so no more than one site is feasible in production. The method of U.S. Ser. No. 09/274,821 is then calibrated at the reference site and used to measure uniformity over the whole wafer.

A dose measurement method of the prior art (e.g. practiced by apparatus sold by Therma-Wave or Boxer Cross) that is sensitive to both implant dose and energy can be used with a calibration measurement made by another device. For example, a SIMS profile may be used to determine the dose and energy at a single point, followed by fitting the as-implanted profile to models of ion implantation profiles as a function of dose and energy (energy effects the depth of the profile, dose the amplitude of the profile) It can then be assumed that the energy is constant across the wafer and dose variation across the wafer can be measured.

Therefore, the invention enables use of a second measurement that has desirable features (e.g. spatial resolution, throughput, sensitivity not available from the first measurement. The invention may also be used in cases where the second measurement requires additional information available only from the first measurement).

Moreover, measurements of the type described herein can be made at the same location or at different locations, depending on the implementation. When made in different locations, the locations may be selected to be optimum for a process that is to be used at that location. For example, a low-resolution process may be used in an area that has no pattern and a high-resolution process may be used in an area having a pattern.

In one embodiment, the locations are sufficiently close to one another so that a number of properties of the workpiece, other than a property of interest (such as thickness of the topmost layer), remain substantially identical (e.g. vary by less than 1%) between the locations, while the property of interest is substantially different (e.g. changes by more than 1%). However, multiple properties of the workpiece in two locations at which measurements are performed need not be substantially identical, e.g. if a rate of change of such properties is known, e.g. from low-resolution measurements at the two locations.

Therefore, numerous such modifications and adaptations of the above-described embodiments, implementations, and examples are encompassed by the attached claims.

What is claimed is:

1. A method of determining a property of a wafer, the method comprising:

measuring reflectance of the wafer at a plurality of wavelengths, based on illumination of the wafer with a beam of white light of a first spot size;

based on reflectance at the plurality of wavelengths, generating a model of reflectance at a predetermined wavelength as a function of thickness of a top layer of the wafer;

measuring reflectance at the predetermined wavelength, based on illumination of the wafer with at least a laser beam of a second spot size, the second spot size being smaller than the first spot size; and based on reflectance at the predetermined wavelength, looking up the model to determine a value of thickness of the top layer of said wafer.

2. The method of claim 1 wherein:

the second measurement obtained by using the laser beam of the second spot size has a higher resolution than the first measurement obtained by using the beam of the first spot size.

3. The method of claim 1 wherein:

the wafer comprises a plurality of areas of integrated circuits separated from one another by a plurality of streets; and a first location illuminated by the beam of the first spot size is in a street in the plurality of streets, and a second location illuminated by the laser beam of the second spot size is in an area in the plurality of areas of integrated circuits.

4. The method claim 1 wherein:

the wafer comprises a semiconductor substrate and a plurality of layers formed on the semiconductor substrate, said plurality of layers including said top layer;

a first measurement obtained by using the beam of the first spot size is of reflectance of at least one dielectric layer at a first location in the wafer; and a second measurement obtained by using the laser beam of the second spot size is of reflectance of said at least one layer in a second location in the wafer;

wherein the second measurement is used to detect thickness of a topmost layer.

5. The method claim 1 wherein:

the workpiece comprises a wafer including a semiconductor substrate and a plurality of layers formed on the semiconductor substrate, said plurality of layers including said top layer;

said top layer is a semiconductor layer; and a measurement, obtained by using the laser beam of the second spot size, is performed in a device that measures junction depth of the top layer in the wafer.

6. The method claim 1 wherein:

the workpiece comprises a wafer including a semiconductor substrate and a plurality of layers formed on the semiconductor substrate, said plurality of layers including said top layer;

said top layer is a semiconductor layer; and a measurement, obtained by using the laser beam of the second spot size, is performed in a device that measures concentration or concentration profile of dopants in the top layer in the wafer.

7. The method of claim 1 wherein:

the laser beam of the second spot size is of constant power; and a pump beam is coincident with said laser beam, the pump beam has a wavelength different from said laser beam, and the pump beam is modulated at a predetermined frequency; and said measuring of reflectance at the predetermined wavelength comprises using a lock-in amplifier at the predetermined frequency.

8. The method of claim 1 wherein:

the top layer is hereinafter "first layer," said model is hereinafter "first model," and said value is hereinafter "first value";

the method further comprises determining a second value of thickness of the first layer based on reflectance at the plurality of wavelengths, generating a second model of reflectance at the predetermined wavelength as a function of thickness of a second layer of the wafer and looking up the second model to determine a third value of thickness of the second layer if the first value is greater than the second value by a predetermined amount.

9. The method of claim 8 wherein:

the predetermined amount is 1%.

10. The method of claim 1 wherein:

reflectance at the plurality of wavelengths is measured at a first location;

reflectance at the predetermined wavelength is measured at a second location; and the second location is separated from the first location by a predetermined distance.

11. The method of claim 10 wherein:

the predetermined distance is sufficiently small to ensure that a plurality of properties, other than said thickness, are substantially identical between said first location and said second location.

* * * * *